US012695812B2

(12) United States Patent
Soza et al.

(10) Patent No.: US 12,695,812 B2
(45) Date of Patent: Jul. 28, 2026

(54) COMMUNICATION PLATFORM FOR QUERYING, FILTERING AND REAL-TIME VIEWING

(71) Applicant: CAREMINDR Corporation, Los Gatos, CA (US)

(72) Inventors: Harry Raymond Soza, San Jose, CA (US); Irina Yermilov, Los Angeles, CA (US); Randall Edwin Coatney, Lafayette, CO (US)

(73) Assignee: CAREMINDER Corporation, Los Gatos, CA (US)

( * ) Notice: Subject to any disclaimer, the term of this patent is extended or adjusted under 35 U.S.C. 154(b) by 221 days.

(21) Appl. No.: 18/603,092

(22) Filed: Mar. 12, 2024

(65) Prior Publication Data

US 2025/0294080 A1     Sep. 18, 2025

(51) Int. Cl.
| | |
|---|---|
| *H04L 67/55* | (2022.01) |
| *G06F 16/335* | (2019.01) |
| *G06F 16/34* | (2025.01) |
| *G16H 20/00* | (2018.01) |
| *H04L 51/42* | (2022.01) |
| *H04L 67/306* | (2022.01) |

(52) U.S. Cl.
CPC ............ *H04L 67/55* (2022.05); *G06F 16/335* (2019.01); *G06F 16/345* (2019.01); *G16H 20/00* (2018.01); *H04L 51/42* (2022.05); *H04L 67/306* (2013.01)

(58) Field of Classification Search
CPC ............................... H04L 67/12; G16H 20/00
See application file for complete search history.

(56) References Cited

U.S. PATENT DOCUMENTS

| | | | | |
|---|---|---|---|---|
| 10,972,891 | B2 * | 4/2021 | Will, IV | ................ G16H 20/10 |
| 11,244,767 | B1 * | 2/2022 | Morrison | ............... G06Q 20/14 |
| 2015/0371176 | A1 * | 12/2015 | Barrett | ............... G06Q 10/0631 |
| | | | | 705/2 |
| 2017/0046753 | A1 * | 2/2017 | Deupree, IV | ........... H04L 67/52 |
| 2021/0391083 | A1 * | 12/2021 | Moturu | .................. G09B 19/00 |
| 2024/0252123 | A1 * | 8/2024 | Berlin | .................. A61B 5/0022 |
| 2025/0097292 | A1 * | 3/2025 | Sheikh | .................... G10L 15/22 |

* cited by examiner

*Primary Examiner* — Kostas J Katsikis

(57)                     ABSTRACT

An example operation may include one or more of receiving registration data from a software application installed on a user device, where the software application is hosted by a host platform, determining a communication sequence for a user of the user device which includes multiple communications spaced apart by intervals of time based on the registration data received from the software application, executing a time-to-live job for the user which includes a timer that is based on the intervals of time included in the communication sequence, and transmitting communications to the user device at the intervals of time based on time elapsing on the timer included in the TTL job.

18 Claims, 18 Drawing Sheets

600A                    FIG. 6A
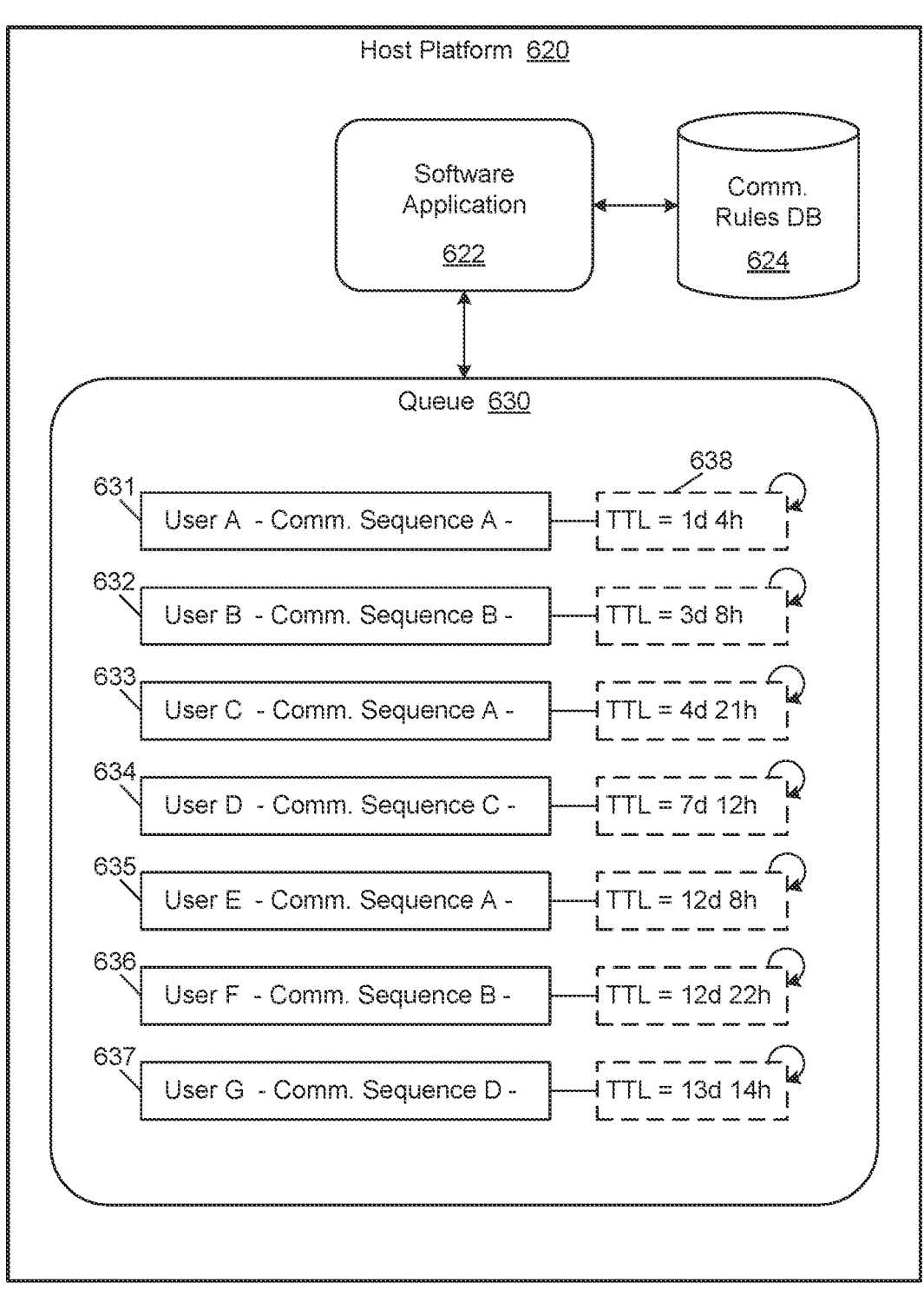

Figure 6B:
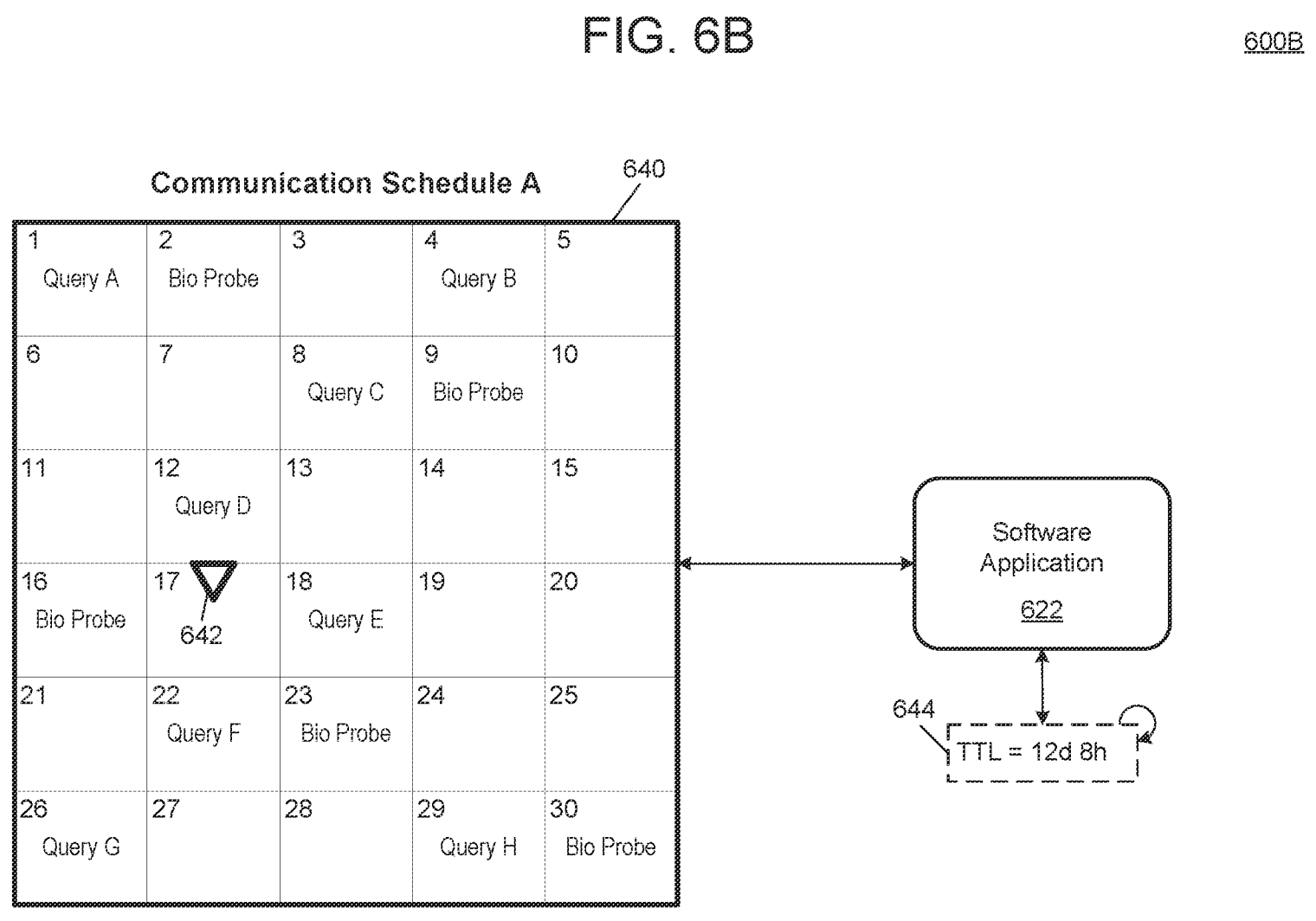

Communication Schedule A    640

| 1 Query A | 2 Bio Probe | 3 | 4 Query B | 5 |
| 6 | 7 | 8 Query C | 9 Bio Probe | 10 |
| 11 | 12 Query D | 13 | 14 | 15 |
| 16 Bio Probe | 17 △ 642 | 18 Query E | 19 | 20 |
| 21 | 22 Query F | 23 Bio Probe | 24 | 25 |
| 26 Query G | 27 | 28 | 29 Query H | 30 Bio Probe |

Software Application 622

644    TTL = 12d 8h

Figure 6D:
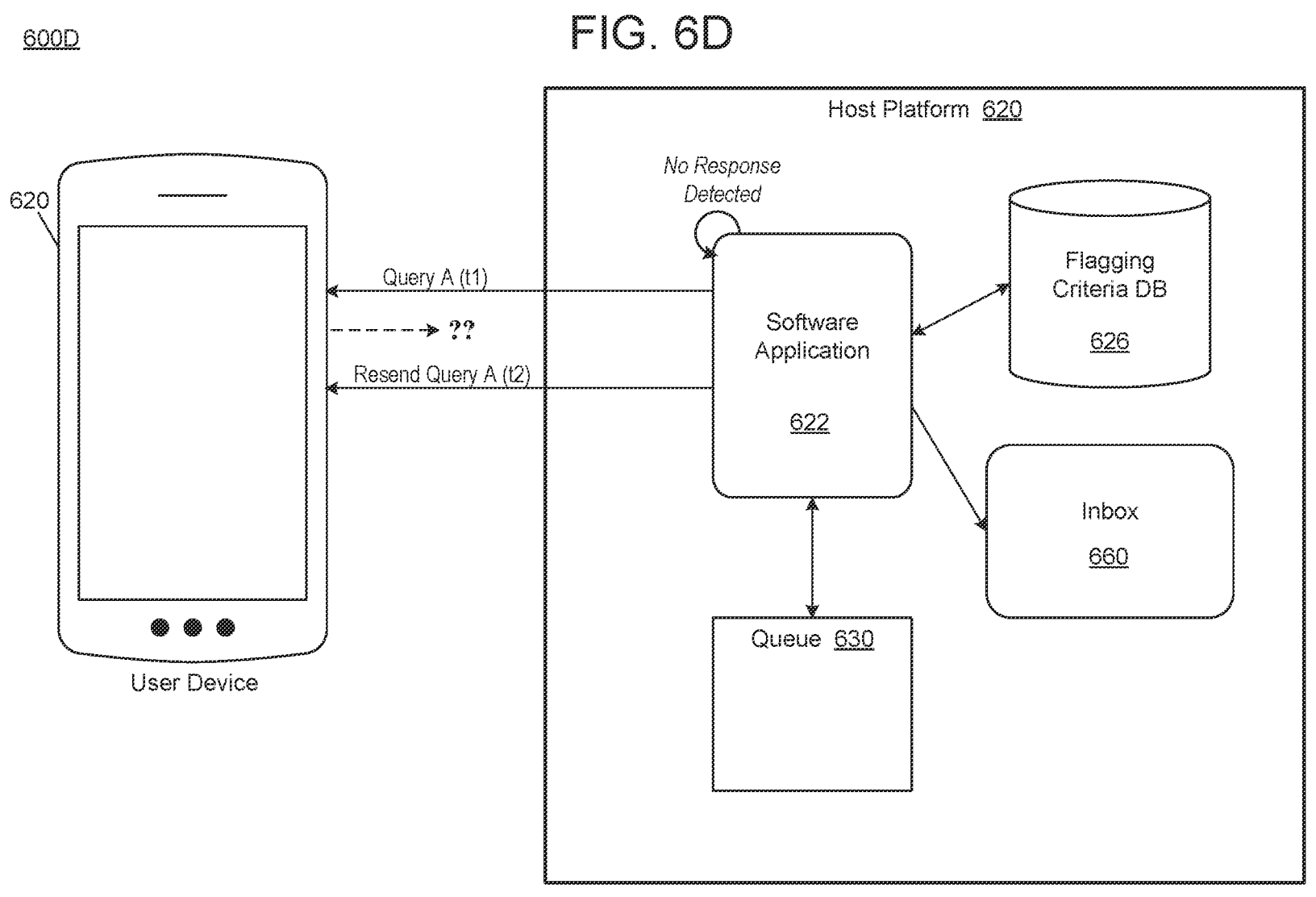

Host Platform 620

Flagging Criteria DB
626

Inbox
660

Software Application
622

Queue 630

No Response Detected

Query A (t1)

??

Resend Query A (t2)

User Device

Figure 6E:
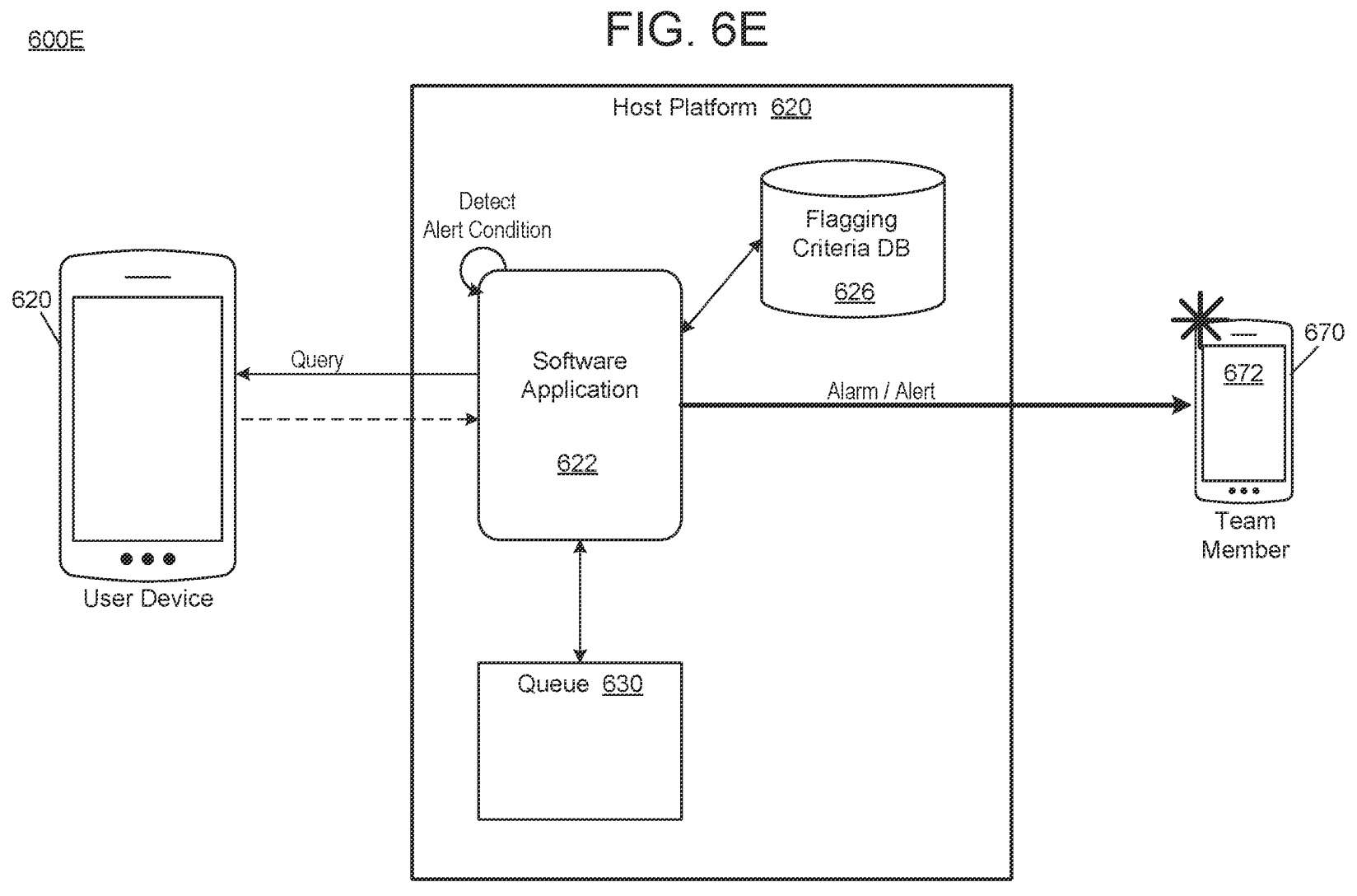

Host Platform 620

Flagging Criteria DB 626

Software Application 622

Queue 630

Detect Alert Condition

Alarm / Alert

Query

User Device

620

Team Member

Figure 8:
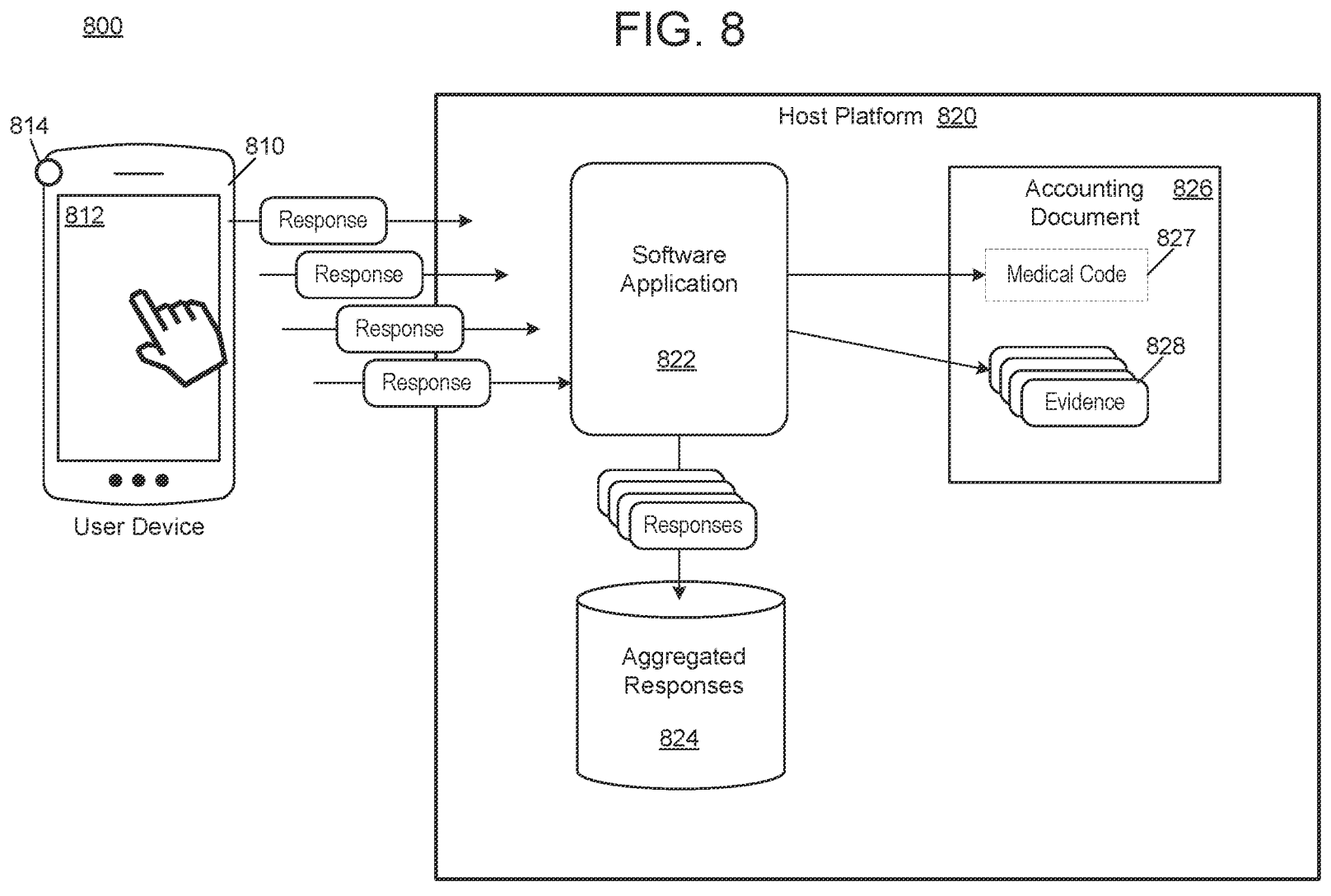

User Device

Response

Response

Response

Response

Host Platform  820

Software
Application

822

Responses

Aggregated
Responses

824

Accounting
Document   826

827

Medical Code

828

Evidence

<u>900</u>                    FIG. 9

Receiving Registration Data from a User Device                    901

Determining a Communication Sequence for the User Device based on the Registration Data                    902

Executing a TTL Job for the User Device which Includes a Timer                    903

Transmitting Communications to the User Device at Intervals of Time based on the Communication Sequence and the Timer                    904

COMMUNICATION PLATFORM FOR QUERYING, FILTERING AND REAL-TIME VIEWING

BACKGROUND

When a patient leaves a medical provider's office, they are often given specific instructions to follow for a predetermined period of time, indefinitely, and even permanently. In the healthcare industry, these specific directions are commonly referred to as a patient's prescribed "care plan". A large medical provider may service thousands of patients on a regular basis. Ensuring that each patient follows the instructions given is a difficult task. Furthermore, communicating with a patient when they are not in the medical provider's office is difficult and often requires staff and medical personnel to reach out directly to the patient. Recently, medical providers have begun offering mobile applications, websites, and the like, to help facilitate appointment registration. However, the application and websites cannot monitor the patient.

SUMMARY

One example embodiment provides an apparatus that may include a memory, and a processor coupled to the memory, where the processor may be configured to receive registration data from a software application installed on a user device, where the software application is hosted by a host platform, determine a communication sequence for a user of the user device which includes multiple communications spaced apart by intervals of time based on the registration data received from the software application, execute a time-to-live (TTL) job for the user which includes a timer that is based on the intervals of time included in the communication sequence, and transmit communications to the user device at the intervals of time based on time elapsing on the timer included in the TTL job.

Another example embodiment provides a method that includes one or more of receiving registration data from a software application installed on a user device, where the software application is hosted by a host platform, determining a communication sequence for a user of the user device which includes multiple communications spaced apart by intervals of time based on the registration data received from the software application, executing a time-to-live job for the user which includes a timer that is based on the intervals of time included in the communication sequence, and transmitting communications to the user device at the intervals of time based on time elapsing on the timer included in the TTL job.

A further example embodiment provides a computer-readable medium comprising instructions, that when read by a processor, cause the processor to perform one or more of receiving registration data from a software application installed on a user device, where the software application is hosted by a host platform, determining a communication sequence for a user of the user device which includes multiple communications spaced apart by intervals of time based on the registration data received from the software application, executing a time-to-live job for the user which includes a timer that is based on the intervals of time included in the communication sequence, and transmitting communications to the user device at the intervals of time based on time elapsing on the timer included in the TTL job.

BRIEF DESCRIPTION OF THE DRAWINGS

FIGS. 3A-3C are diagrams illustrating processes for training an artificial intelligence (AI) model according to example embodiments.

FIG. 4 is a diagram illustrating a process of prompting an AI model to generate an architecture diagram according to example embodiments.

FIGS. 6A-6E are diagrams illustrating a process of managing a lifecycle of a communication sequence with a user device according to example embodiments.

FIG. 8 is a diagram illustrating a process of generating an evidence-based accounting report for a provider according to example embodiments.

DETAILED DESCRIPTION

It is to be understood that although this disclosure includes a detailed description of cloud computing, implementation of the teachings recited herein is not limited to a cloud computing environment. Rather, embodiments of the instant solution are capable of being implemented in conjunction with any other type of computing environment now known or later developed.

The example embodiments are directed to a host platform that can query users via user devices, track the status of the users based on responses from the user devices, identify urgent users that are of higher priority than other users based on the responses, and provide an external system with an inbox-view of a summary of the status of the users. In some embodiments, the host platform may arrange multiple summaries of multiple users within the same inbox view based on different priorities of the user. This enables a viewer of the external system to identify which users are in more need of help, and which users are not in need of help. In this way, the host platform may perform the role of a "watch tower" for an external provider of many different users by probing the users for information including descriptions, answers, biometric readings, and the like.

According to various embodiments, the responses from each user can be analyzed by the host platform to determine which users are in most need of help, and which users are not in need of help. The host can provide a provider (such as a medical provider) with an inbox view of the status of all of the users associated with that provider, while highlighting the users that are in the most need of help. Furthermore, by probing the users, the host platform can ensure that a sequence of communication continues for the user after they leave the service provider (such as a medical provider). In other words, the host platform can ensure that the user adheres to a schedule that the user was assigned by the medical provider.

Figure 1:
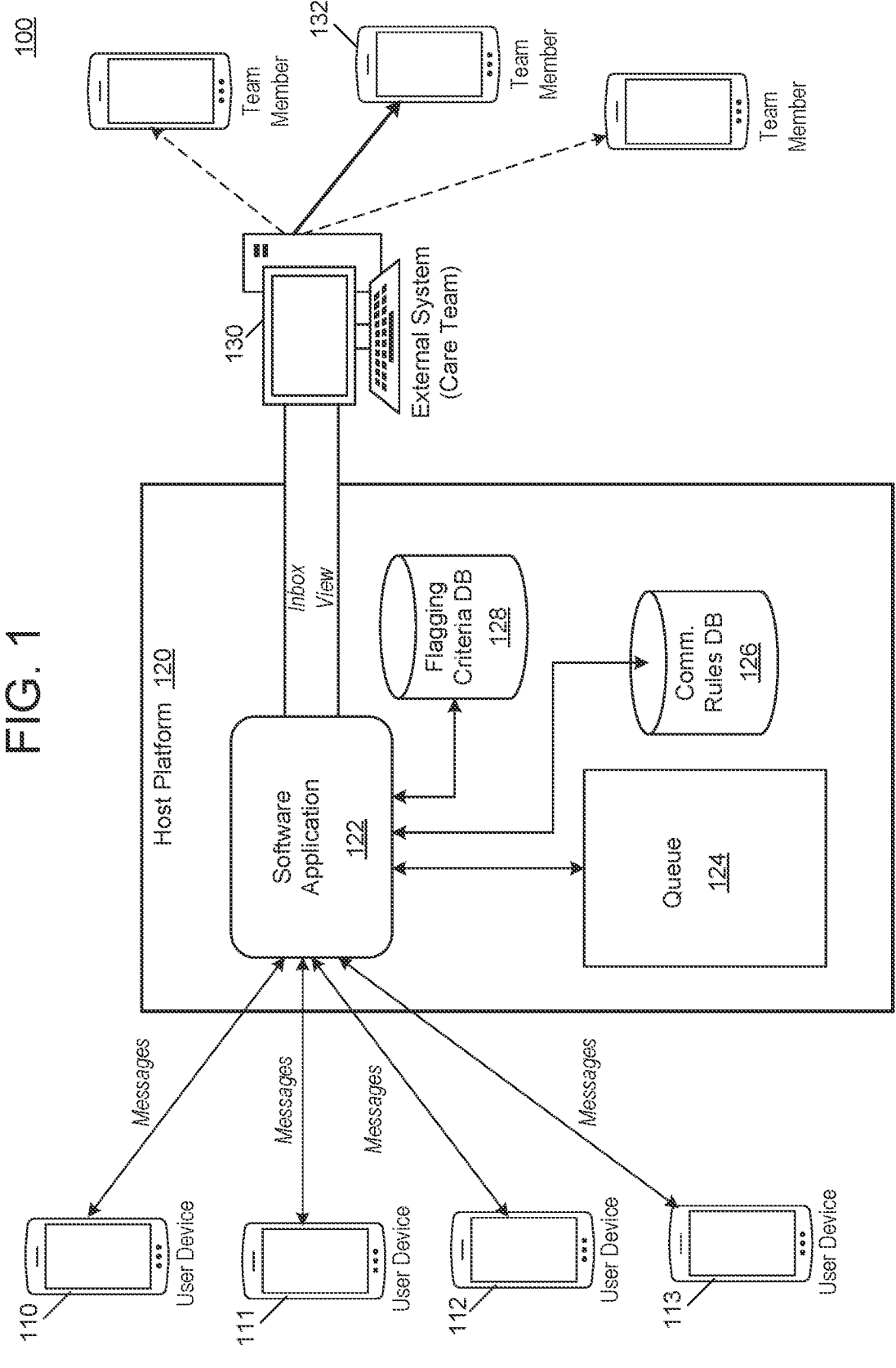
FIG. 1 is a diagram illustrating a platform for querying user devices, filtering responses from the user devices, and providing a real-time interface for viewing the filtered responses according to example embodiments.

FIG. 1 illustrates a host platform 120 for querying user devices, filtering responses from the user devices, and providing a real-time interface for viewing the filtered responses according to example embodiments. In the example embodiments, the host platform 120 may be a cloud platform, a web server, a database, a combination of devices, and the like. Here, the host platform 120 may host a software application 122 that is capable of querying user devices, such as user devices 110, 111, 112, and 113, for status information. Here, each user device may download and install a front-end of the software application 122 to the respective device which enables the user device to communicate with the software application 122 (e.g., backend) on the host platform 120. In some embodiments, the user devices may be mobile devices such as smartphones, smart wearables, tablets, laptops, and the like.

According to various embodiments, the software application 122 may transmit in-app communications/messages to the user devices with request for information. As an example, the messages may include a question (such as a YES/NO question, a multiple-choice question, etc.) for the user to answer. As another example, the querying may include querying the user device for a biometric reading, a description of symptoms, or the like. In response, the user devices may return responses that are analyzed the software application 122 to determine statuses of the users. Each user device may be assigned a respective communication sequence, for example, based on an underlying condition of the user (e.g., Covid, hypertension, heart disease, diabetes, chronic obstructive pulmonary disease, sleep apnea, and the like). The communication sequence may encourage "adherence" to a prescribed care plan. The care plan may include actions that the patient is to perform, medications the patient is to take, steps the patient is to take at home, and the like. The care plan may be prescribed by a medical provider of the patient. The communication sequence may include questions, prompts, etc., which both encourage the patient to adhere to the prescribed care plan and track whether the patient has performed the actions required by the care plan. Furthermore, each user's communication sequence may include a respective lifecycle that begins when that user registers. Therefore, each user's communication sequence may be managed separately using a queue 124, communication rules stored in a communications database 126, and the like.

The responses provided from the user devices may be analyzed for urgency/priority attributes, and in some cases, the user responses may be flagged based on criteria included in a flagging criteria database 128. Each query/response may include its own flagging criteria that can be analyzed by the software application 122 to identify whether or not to attach a flag to a summary, and what type of flag should be attached.

The software application 122 may generate an inbox that includes "summaries" of each of the users of a particular medical facility and display the inbox to an external computing system of a staff member or medical professional of the medical facility. The inbox may include summaries of the current status of the users that have been queried that day, and previous days. The summaries may also include flags added by the software application 122 depending on the urgency/priority of the status. The summaries may be arranged within the inbox such that the most urgent summaries are placed at the top of the inbox or somewhere where the user will quickly notice the urgency of the user. A view of the inbox may be output to an external system 130 such as a cohort, staff member, etc. of a care team. In response, an administrator of the external system 130 may identify a team member and transmit a notification to the team member for further care. In the example of FIG. 1, the external system 130 transmits a message to a team member device 132 with a request to pick-up a patient and bring them to a medical provider.

According to various embodiments, the provider may include a team of people such as assistants, nurses, pharmacists, drivers to get people to the appointment, etc. The probing performed by the software application 122 can identify when someone needs help. Furthermore, an assistant using the external system 130 can identify the team member that can help the patient. Here, the provider may be responsible for a large number of patients (e.g., hundreds, thousands, etc). The system can provide significant benefits in a large community setting with a great deal of patients by quickly identifying the patients that are in urgent need, and finding the correct resources/team members to help them in a very fast manner. The assistant managing the inbox view on the external system 130 may follow a protocol based on the problem. Here the assistant may play the role of a navigator that quickly identifies how to respond and which team member needs to respond and contact the team member.

In some embodiments, the software application 122 may analyze a response or a group of responses from a user with an artificial intelligence (AI) model to identify a status of the user that is only detectable after a prolonged period of time. For example, one response with an elevated reading that dissipates by the next response, may not draw an alert flag. However, if the same patient experiences multiple ups-and-downs with their status, this may indicate a more serious condition that can be detected by the AI model.

In one embodiment, the system entails the development of a Remote Patient Monitoring (RPM) Wearable system to enhance healthcare delivery by continuously monitoring patient's health parameters outside of traditional clinical settings. The RPM Wearable system comprises a wearable device equipped with sensors capable of monitoring vital signs such as heart rate, blood pressure, oxygen saturation, and activity levels in real-time. These sensors seamlessly communicate with a companion mobile application installed on the user's smartphone or tablet, which serves as the interface for data collection and interaction with the system. The mobile app features a user-friendly interface where patients can view their health data, receive personalized notifications, and communicate with healthcare providers. Upon setup, users input their medical history, current health condition, and any prescribed care plans into the mobile application. This registration data serves as the basis for determining each user's personalized communication sequence, tailored to their specific health needs and care requirements. Based on this communication sequence, the system then executes a time-to-live (TTL) job, setting intervals for sending reminders, educational materials, and alerts to the user's device. For instance, a patient with hypertension might receive reminders to measure their blood pressure at specific times throughout the day, take their prescribed medication, engage in physical activity, and follow dietary recommendations. These reminders would be sent at intervals determined by the TTL job, ensuring timely and consistent communication with the user. Additionally, the system analyzes the user's health data in real-time to detect any deviations from their baseline parameters or concerning trends, triggering immediate alerts or interventions as needed. The centralized platform supporting the RPM Wearable system is crucial in aggregating and analyzing the vast amounts of data generated by users' wearable devices. Advanced analytics and machine learning algorithms are employed to identify patterns, predict health risks, and provide patients and healthcare providers personalized insights. Moreover, the platform enables remote monitoring by clinicians, allowing them to review patients' health data, track their progress, and intervene proactively when necessary.

In one embodiment, the system supports aging individuals living independently at home while providing peace of mind to their caregivers. At its core, the system integrates smart home technology, wearable devices, and a dedicated mobile application to monitor the daily activities and health status of elderly users. Smart sensors strategically placed throughout the home detect movement patterns, door openings, and appliance usage, providing valuable insights into the user's routine and identifying any deviations or anomalies that may indicate potential health concerns or emergencies. Additionally, in real-time, wearable devices equipped with sensors for tracking vital signs and physical activity continuously monitor the user's health parameters, such as heart rate, sleep patterns, and activity levels. The companion mobile application is the central hub for users to access their health data, receive personalized notifications, and communicate with caregivers or emergency responders. During the initial setup, users provide relevant medical history, emergency contacts, and preferences, which inform the system's algorithms in creating a personalized care plan tailored to each user's unique needs and preferences. This registration data serves as the basis for determining the user's communication sequence, which dictates the frequency and type of interactions between the system and the user. The system employs a time-to-live (TTL) job mechanism to execute the communication sequence, ensuring timely delivery of reminders, alerts, and wellness checks to the user's mobile device or designated caregiver. For instance, the system may send reminders for medication intake, hydration, or daily exercise routines at predetermined intervals throughout the day, helping users adhere to their prescribed care plans and maintain their overall health and well-being. Moreover, the system's intelligent algorithms analyze the user's health data in real time, detecting any concerning trends or deviations from their baseline parameters and triggering immediate alerts or interventions if necessary. One of the system's key features is its ability to provide remote monitoring capabilities to caregivers and healthcare providers. Through a secure web portal or mobile application, caregivers can access real-time updates on the user's health status, review activity logs, and receive alerts for critical events or emergencies. This enables caregivers to provide timely assistance, coordinate care with other family members or healthcare professionals, and intervene proactively to ensure the user's safety and well-being.

In one embodiment, the system introduces a robust chronic disease management platform designed to address the complex needs of patients living with chronic conditions such as diabetes, hypertension, or COPD. At its core, the platform integrates electronic health records (EHR), wearable devices, and a dedicated mobile application to enable continuous monitoring, personalized care planning, and proactive intervention for patients with chronic diseases. The platform's seamless integration with EHR systems allows healthcare providers to access comprehensive patient data, including medical history, lab results, and treatment plans, facilitating informed decision-making and personalized care delivery. Patients interact with the platform through a user-friendly mobile application, where they can input relevant health information, track their symptoms, and receive customized recommendations and interventions based on their individual health needs and care goals. During the initial setup, patients provide information about their chronic condition, medication regimen, lifestyle factors, and preferences, which inform the platform's algorithms in creating a tailored care plan tailored to their specific needs and preferences. The system employs a time-to-live (TTL) job mechanism to execute the communication sequence, ensuring timely delivery of reminders, educational materials, and alerts to patients' mobile devices. For example, patients with diabetes may receive reminders for blood glucose monitoring, medication adherence, dietary recommendations, and physical activity goals at specific intervals throughout the day, helping them manage their condition effectively and prevent complications. The platform's advanced analytics capabilities analyze patients' health data in real-time, detecting trends, identifying risk factors, and predicting potential health issues before they escalate. Healthcare providers leverage actionable insights to adjust treatment plans, provide targeted interventions, and engage patients in proactive self-management strategies, ultimately improving health outcomes and reducing healthcare costs associated with chronic disease management. A key strength of the system is its ability to facilitate remote monitoring and virtual care delivery, enabling patients to receive timely support and intervention from their healthcare team without the need for frequent in-person visits. Through secure messaging, telehealth consultations, and remote monitoring tools, patients can communicate with their healthcare providers, receive personalized guidance, and access resources to support their self-management efforts from their homes.

In one embodiment, the system introduces a post-surgery rehabilitation assistant system tailored to support patients following orthopedic procedures or surgeries during their recovery. The system combines wearable sensors, a mobile application, and a cloud-based platform to provide personalized guidance, feedback, and monitoring throughout rehabilitation. Patients wear sensors on their bodies or attach them to their rehabilitation equipment, allowing the system to track their movements, range of motion, and adherence to prescribed exercises in real-time. The companion mobile application is a virtual rehabilitation coach, providing patients with instructional videos, exercise demonstrations, and real-time feedback on their technique and performance. Upon setup, patients input details about their surgical procedure, rehabilitation protocol, and any physical limitations or concerns, which inform the system's algorithms in tailoring the rehabilitation program to their specific needs and capabilities. The system employs a time-to-live (TTL) job mechanism to execute the communication sequence, delivering reminders, exercise prompts, and progress updates to patients' mobile devices at appropriate daily intervals. For instance, patients may receive reminders to perform their prescribed exercises, notifications about upcoming physical therapy sessions, and encouragement to stay active and engaged in their recovery process. One of the system's key features is its ability to provide real-time feedback and guidance to patients, helping them perform exercises correctly, avoid potential pitfalls, and progress safely through their rehabilitation program. The system analyzes patients' movement patterns and biomechanics, identifying areas for improvement and providing personalized recommendations for adjustment or modification. The system's cloud-based platform enables healthcare providers to monitor patient's progress remotely, track their adherence to the rehabilitation program, and intervene proactively if any issues or concerns arise. Through secure access to patients' data and real-time communication tools, providers can offer support, answer questions, and adjust treatment plans as needed, ensuring that patients receive comprehensive care and guidance throughout their recovery journey.

In one embodiment, the system is designed to provide ongoing care and assistance to individuals with psychiatric disorders or emotional challenges. The system integrates mood-tracking tools, therapy modules, crisis intervention features, and peer support groups into a user-friendly mobile application, offering users a holistic approach to mental health management and support. Users interact with the platform through the mobile application, where they can track their mood fluctuations, journal their thoughts and feelings, and access a wide range of therapeutic resources and interventions tailored to their specific needs and preferences. Upon registration, users provide information about their mental health history, current symptoms, treatment preferences, and crisis management strategies, which inform the platform's algorithms in creating a personalized care plan and communication sequence. The platform employs a time-to-live (TTL) job mechanism to execute the communication sequence, sending reminders, coping strategies, and wellness tips to users' mobile devices at predetermined daily intervals. A key feature of the system is its real-time chat and video session capabilities, allowing users to connect with licensed therapists, peer support groups, and crisis intervention teams for immediate assistance and guidance during times of distress. The platform's crisis intervention features enable users to access emergency resources, hotlines, and safety plans, empowering them to navigate crisis situations effectively and seek help. Additionally, the platform utilizes advanced analytics and artificial intelligence (AI) algorithms to analyze users' mood data, detect patterns, and identify potential triggers or risk factors for mental health issues. These actionable insights enable the platform to provide users with personalized recommendations, coping strategies, and intervention plans, helping them manage their symptoms, prevent relapse, and improve their overall well-being. The system fosters community and belonging through its peer support groups, where users can connect with others who share similar experiences, offer mutual support, and share coping strategies and resources. By promoting social connection, empathy, and peer support, the platform aims to reduce feelings of isolation and stigma associated with mental illness, empowering users to take control of their mental health and build resilience in the face of adversity.

In one embodiment, the system provides a comprehensive solution for remote patient monitoring and engagement, leveraging digital communication channels to enhance healthcare delivery outside traditional clinical settings. The system includes a software application installed on the user device that facilitates registration and ongoing communication with the host platform. Upon registration, the software application transmits relevant data to the host platform, including user demographics, medical history, and any specific instructions provided by the medical provider. The host platform, equipped with a backend software application, processes the data to formulate a personalized communication sequence for each user. This sequence is designed to prompt users with inquiries, reminders, or educational content related to their prescribed care plan. The communication sequence includes multiple communications spaced apart by intervals of time, which are based on the registration data received from the software application. Subsequently, the system executes a time-to-live (TTL) job for the user, incorporating a timer that is synchronized with the intervals of time specified in the communication sequence. As time progresses according to the TTL job's timer, the processor transmits communications to the user device at the predetermined intervals, ensuring timely and consistent interaction with the user. The TTL job, managed by the system, acts as a scheduler for the communication sequence. It initiates upon registration and progresses through the specified intervals of time, triggering communication events accordingly. These communications take the form of push notifications, in-app messages, or emails delivered to the user's device. The timing of the communications aligns with the intervals established in the user's care plan, ensuring that users receive timely reminders and support to adhere to their prescribed regimen. Throughout the process, the host platform analyzes user responses to gauge adherence and identify any urgent needs. Responses from the user device are received by the host platform, where they are processed and evaluated against predefined criteria. Urgent cases are flagged for immediate attention, while non-urgent responses are managed according to the communication sequence. Additionally, the host platform generates summaries of user statuses, incorporating urgency flags as needed, and presents them in an inbox interface accessible to medical professionals or care team members.

Figure 2:
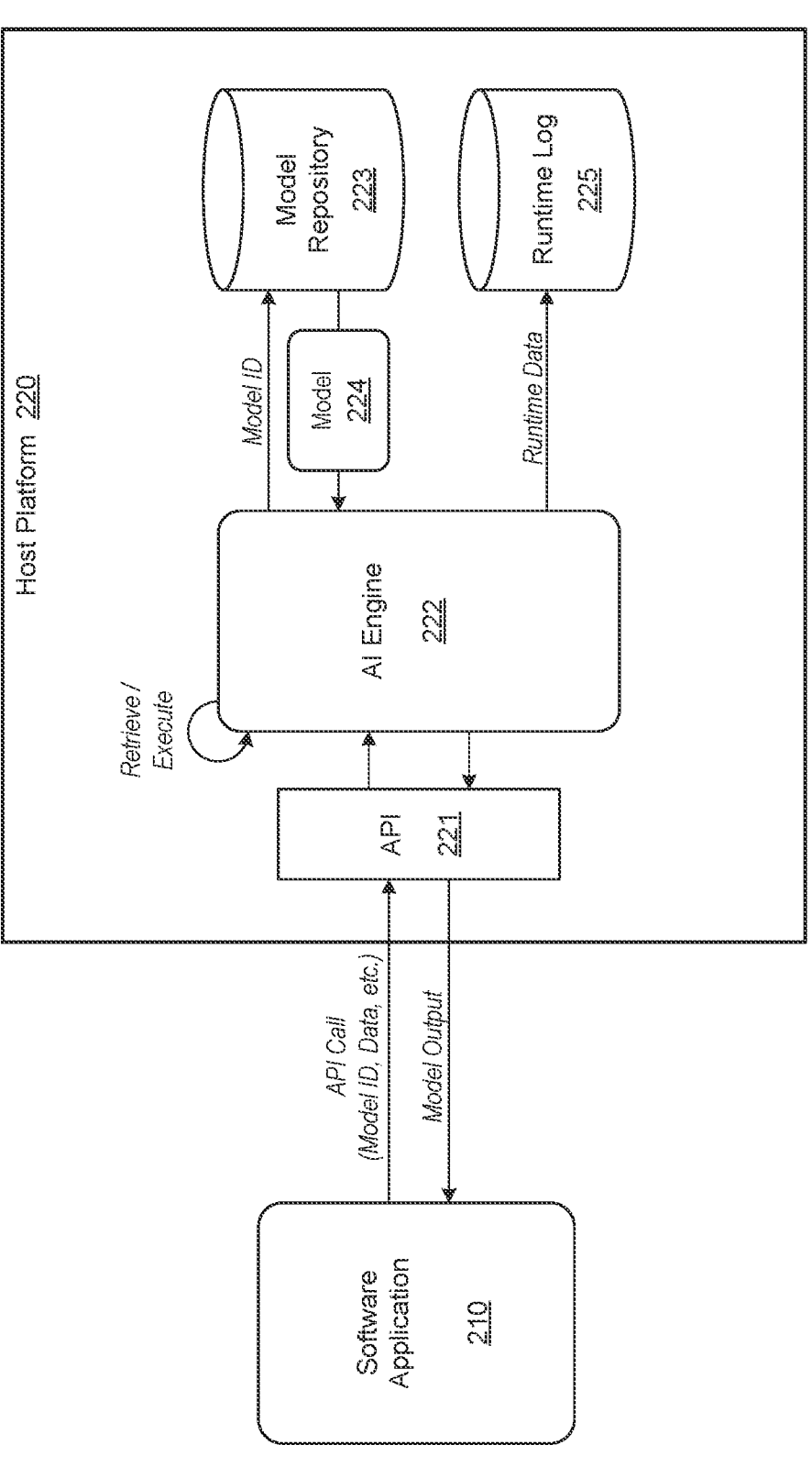
FIG. 2 is a diagram illustrating a process of executing a predictive model on input content according to example embodiments.

In FIG. 2, the AI engine 222 may control access to models that are stored within the model repository 223. For example, the models may include AI models, generative AI models, machine learning models, neural networks, LLMs, and/or the like. The software application 210 may trigger execution of the model 224 from the model repository 223 via submission of a call to an API 221 (application programming interface) of the AI engine 222. The request may include an identifier of the model 224 such as a unique ID assigned by the host platform 220, a payload of data (e.g., to be input to the model during execution), and the like. The AI engine 222 may retrieve the model 224 from the model repository 223 in response, and deploy the model 224 within a live runtime environment. After the model is deployed, the AI engine 222 may execute the running instance of the model 224 on the payload of data, and return a result of the execution to the software application 210.

In some embodiments, the payload of data may be a format that is not capable of being input to the model 224 nor read by a computer processor. For example, the payload of data may be in text format, image format, audio format, and the like. In response, the AI engine 222 may convert the payload of data into a format that is readable by the model 224 such as a vector or other encoding. The vector may then be input to the model 224.

In some embodiments, the software application 210 may display a user interface which enables a user thereof to provide feedback from the output provided by the model 224. For example, a user may input a confirmation about an image/NFT generated by a GenAI model. This information may be added to the results of execution and stored within a log 225. The log 225 may include an identifier of the input, an identifier of the output, an identifier of the model used, and feedback from the recipient. This information may be used to subsequently re-train the model.

Figure 3A:
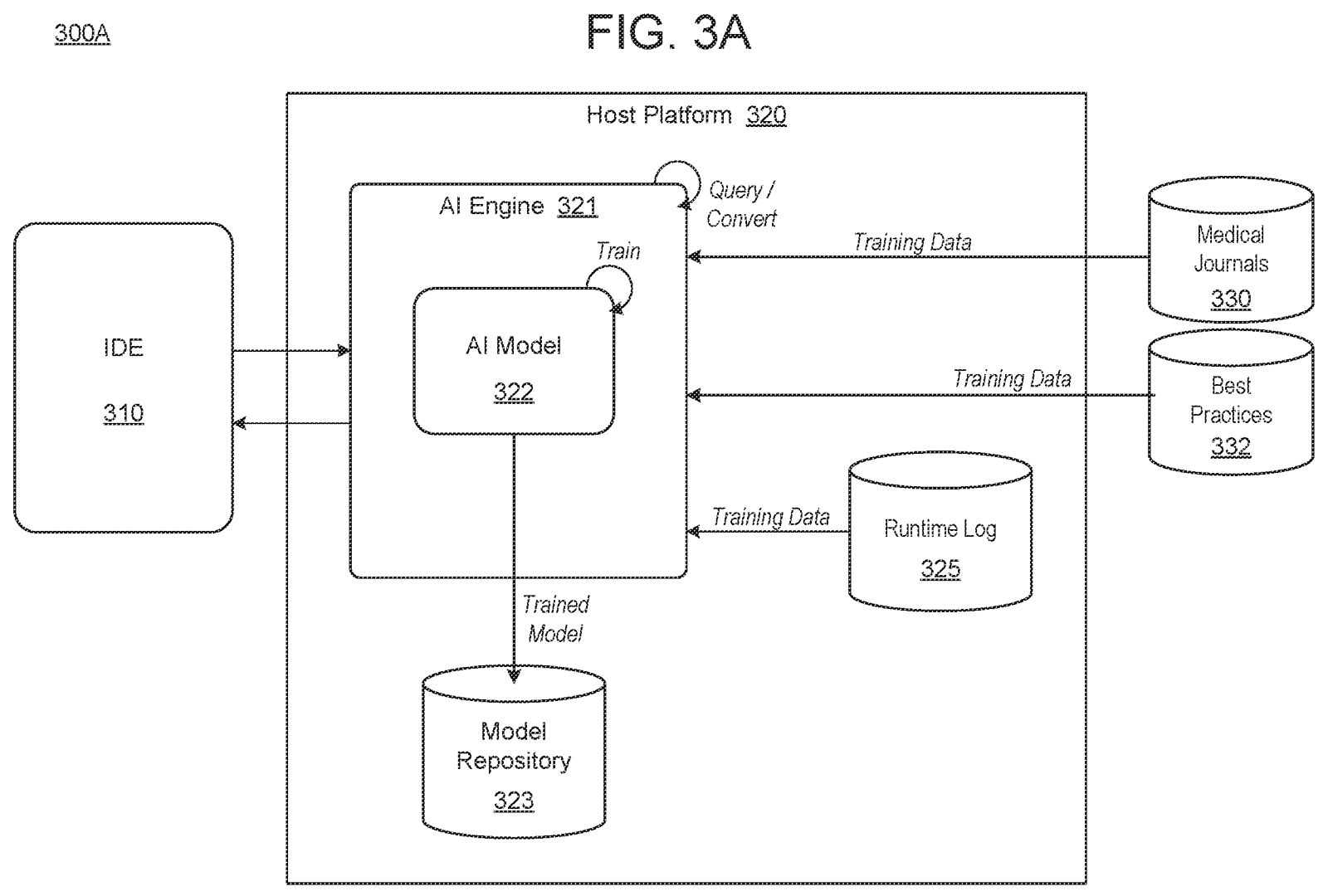

FIG. 3A illustrates a process 300A of training an AI model 322 according to example embodiments. However, it should be appreciated that the process 300A shown in FIG. 3A is also applicable to other types of models such as machine learning models, AI models, and the like. Referring to FIG. 3A, a host platform 320 may host an IDE 310 (integrated development environment) where AI models, machine learning models, generative AI models, and the like may be developed, trained, retrained, and the like. In this example, the IDE 310 may include a software application with a user interface accessible by a user device over a network or through a local connection. For example, the IDE 310 may be embodied as a web application that can be accessed at a network address, URL, etc by a device. As another example, the IDE 310 may be locally or remotely installed on a computing device used by a user.

The IDE 310 may be used to design a model (via a user interface of the IDE), such as a generative artificial intelligence model that can receive text as input and generate custom imagery, etc. The model can then be executed/trained based on the training data established via the user interface. For example, the user interface may be used to build a new model. The training data for training such a new model may be provided from medical standards and other authoritative documents that include a list of steps to perform for specific medical conditions under specific circumstances stored in a medical standards data store 330. As another example, the training data may be provided from a best practices data store 332 which contains the most up-to-date best practices in the medical field for specific health conditions. As another example, the training data may be pulled from one or more other external data stores such as publicly available sites, etc. It can be difficult for a doctor or other medical professional to memorize all the standards and best practices in the medical field. As such, the example embodiments may implement such knowledge within the AI model 322.

During training, the AI model 322 may be executed on training data via an AI engine 321 of the host platform 320. The training data may include a large corpus of text from software tests as well as best practice documentation, medical standards, compliance documentation, and the like. When the model is fully trained, it may be stored within the model repository 323 via the IDE 310, or the like.

As another example, the IDE 310 may be used to retrain the AI model 322 after the model has already been deployed. Here, the training process may use executional results that have already been generated/output by the AI model 322 in a live environment (including any customer feedback, etc.) to retrain the AI model 322. For example, predicted outputs that are custom generated by the AI model 322 and the user feedback of the outputs may be used to retrain the model to further enhance the images that are generated for all users. This data may be captured and stored within a runtime log 325 or other data store within the live environment and can be subsequently used to retrain the AI model 322.

Figure 3B:
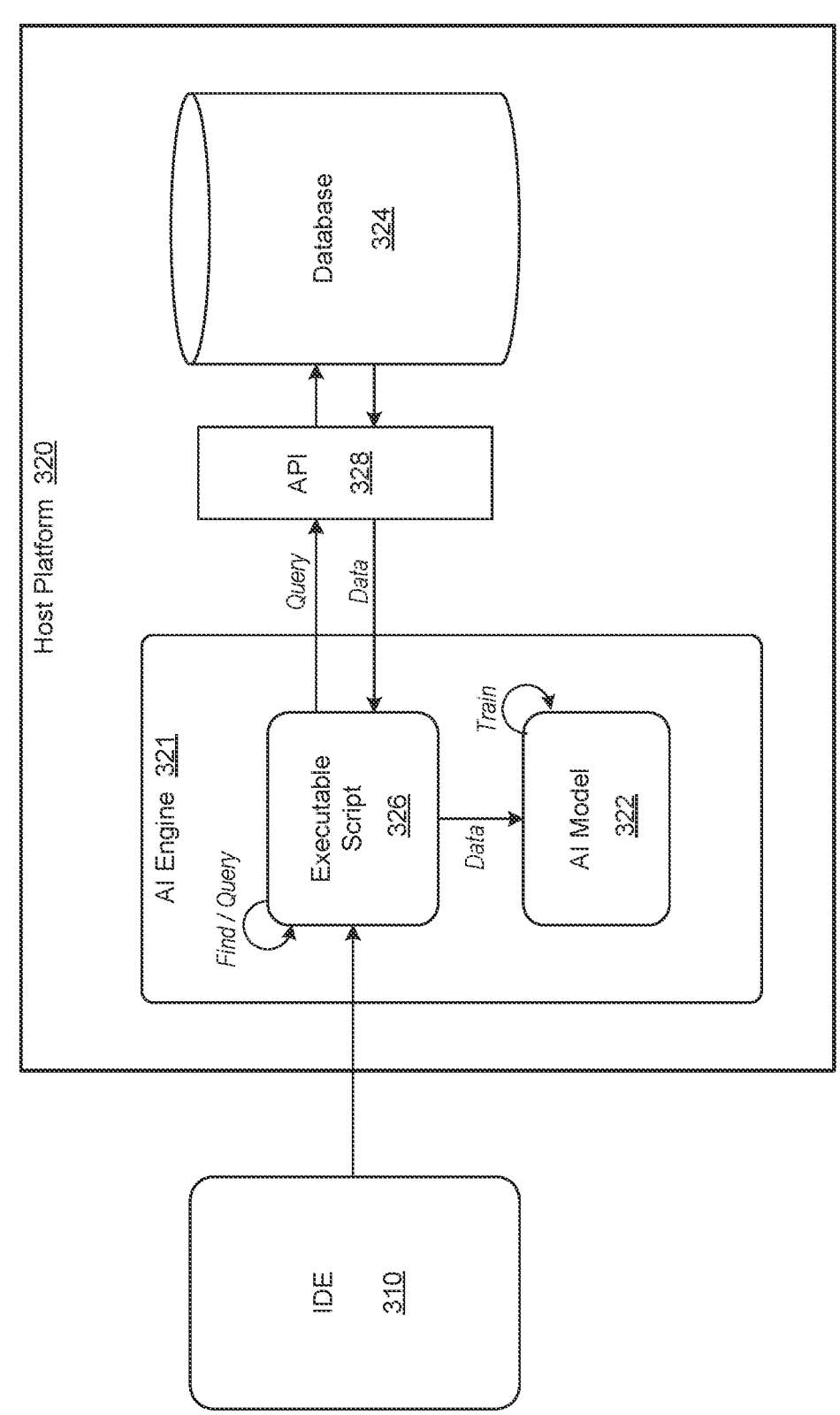

FIG. 3B illustrates a process 300B of executing a training process for training/retraining the AI model 322 via an AI engine 321. In this example, a script 326 (executable) is developed and configured to read data from a database 324 and input the data to the AI model 322 while the AI model is running/executing via the AI engine 321. For example, the script 326 may use identifiers of data locations (e.g., table IDs, row IDs, column IDs, topic IDs, object IDs, etc.) to identify locations of the training data within the database 324 and query an API 328 of the database 324. In response, the database 324 may receive the query, load the requested data, and return it to the AI engine 321 where it is input to the AI model 322. The process may be managed via a user interface of the IDE 310 which enables a human-in-the loop during the training process (supervised learning). However, it should also be appreciated that the system is capable of unsupervised learning as well.

The script 326 may iteratively retrieve additional training data sets from the database 324 and iteratively input the additional training data sets into the AI model 322 during the execution of the AI model 322 to continue to train the AI model 322. The script may continue the process until instructions within the script 326 tell the script 326 to terminate which may be based on a number of iterations (training loops), total time elapsed during the training process, etc.

Figure 3C:
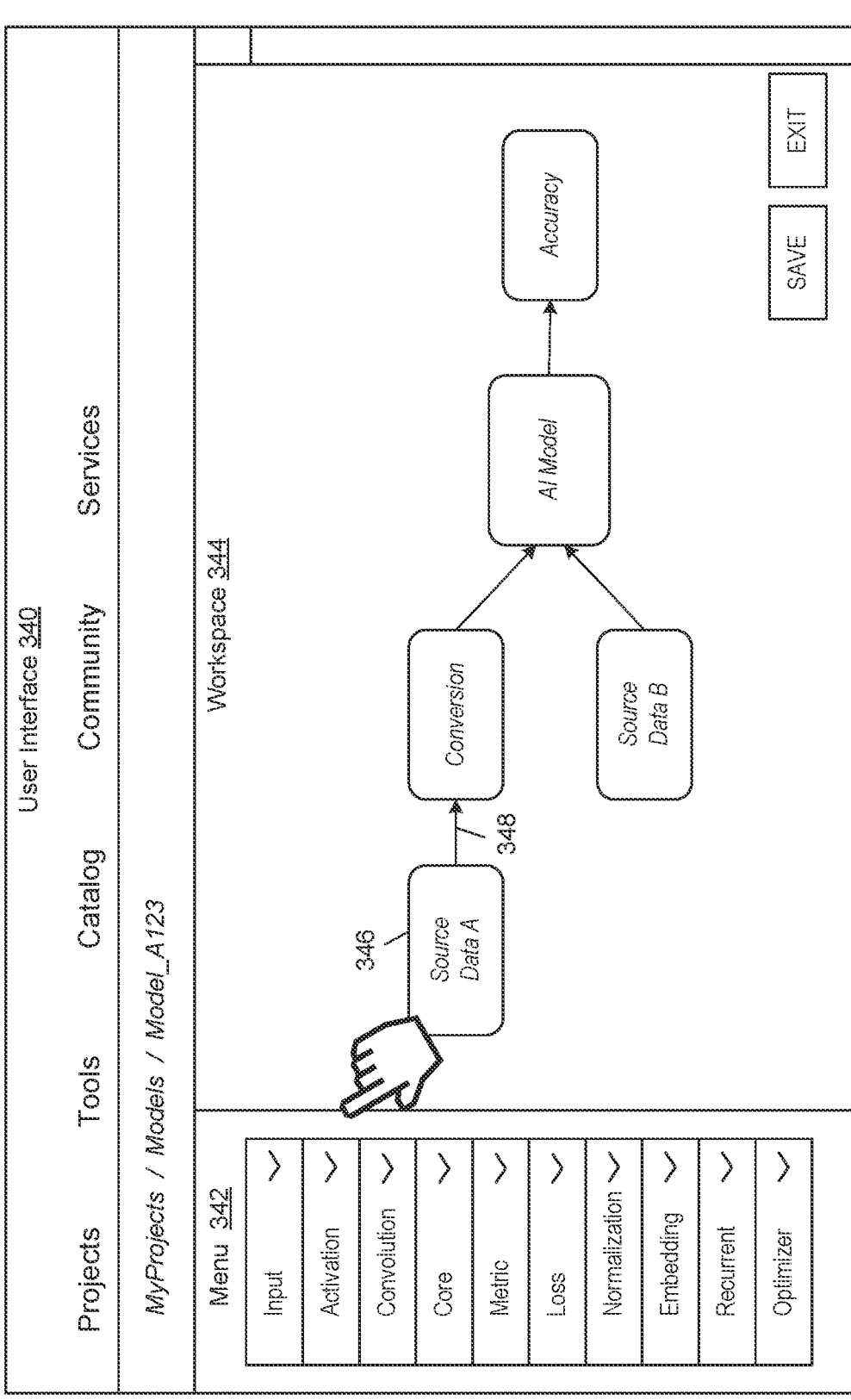

FIG. 3C illustrates a process 300C of designing a new AI model via a user interface 340 according to example embodiments. As an example, the user interface 340 may be output as part of the software application which interacts with the IDE 310 shown in FIG. 3A, however, embodiments are not limited thereto. Referring to FIG. 3C, a user can use an input mechanism to make selections from a menu 342 shown on the left-hand side of the user interface 340 to add pieces to the model such as data components, model components, analysis components, etc. within a workspace 344 of the user interface 340.

In the example of FIG. 3C, the menu 342 includes a plurality of graphical user interface (GUI) menu options which can be selected to drill-down into additional components that can be added into the model design shown in the workspace 344. Here, the GUI menu options include options for adding features such as neural networks, machine learning models, AI models, data sources, conversion processes (e.g., vectorization, encoding, etc.), analytics, etc. The user can continue to add features to the model and connect them using edges or other means to create a flow within the workspace 344. For example, the user may add a node 346 to a diagram of a new model within the workspace 344. For example, the user may connect the node 346 to another node in the diagram via an edge 348 creating a dependency within the diagram. When the user is done, the user can save the model for subsequent training/testing.

According to various embodiments, the AI model described herein may be trained based on custom defined prompts that are designed to draw out specific attributes associated with a unique/custom goal and/or design that is to be generated for a user. These same prompts may be output during live execution of the AI model. For example, a user may input a description of a goal such as a financial amount that needs to be saved and an identifier of the item. The requirements can then be used by the AI model to generate content (e.g., images, text, documents, tickets, web pages, etc.) which represent the goal. The prompts may be generated via prompt engineering that can be performed through the model training process such as the model training process described above in the examples of FIGS. 3A-3C.

Prompt engineering is the process of structing sentences (prompts) so that they are understood by a generative AI model. A prompt may ask for and receive a description of a testing feature to be included in a software test. The text may be input to the generative AI model and used to create a new unique image and/or description. Part of the prompting process may include delays/waiting times that are intentionally included within the script such that the model has time to think/understand the input data.

Figure 4:
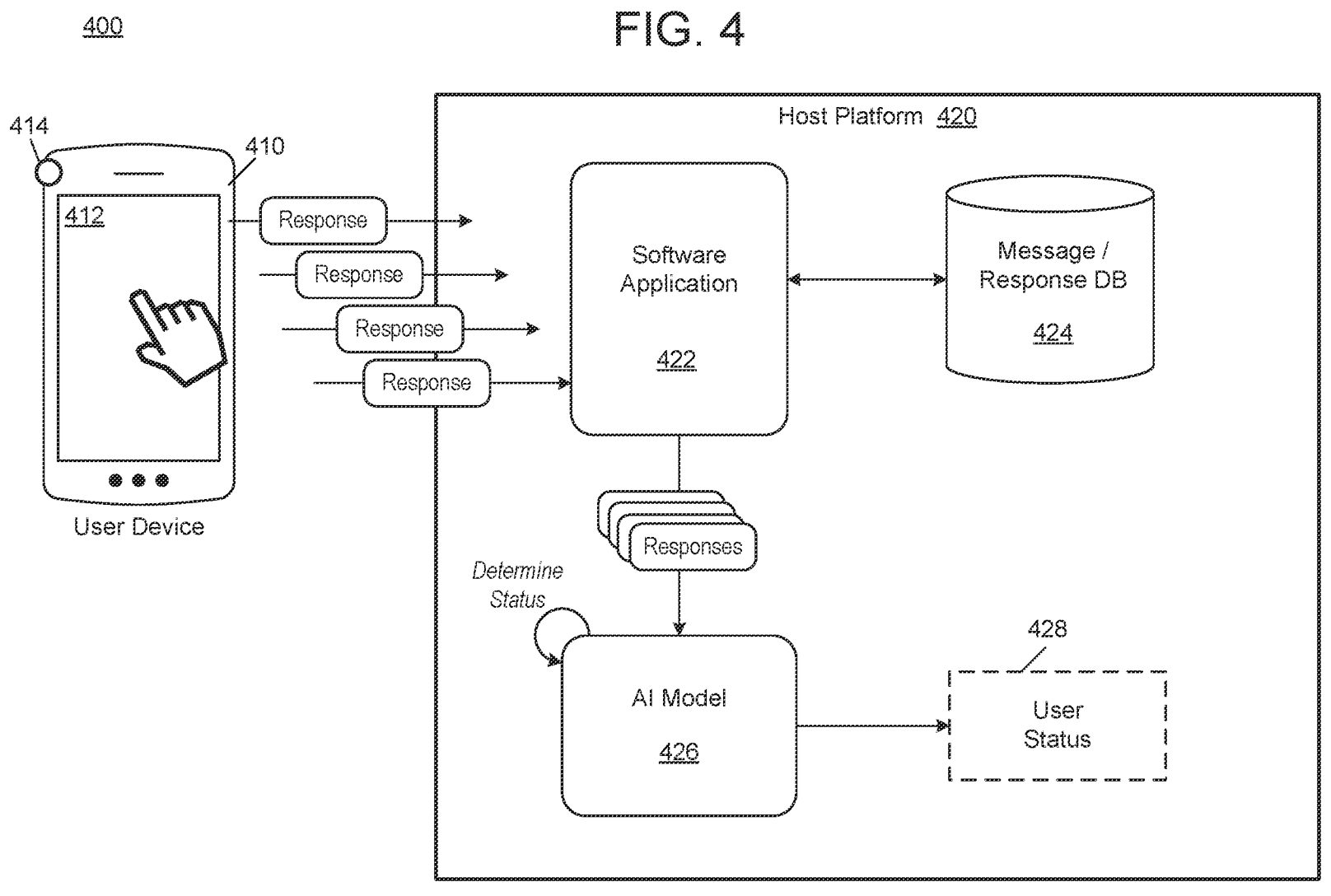

FIG. 4 illustrates a process 400 of an AI model 426 determining a user status (e.g., a degree of urgency, etc.) according to example embodiments. Referring to the example of FIG. 4, a host platform 420 may host a software application 422 that executes a communication sequence with a user device 410. The communication sequence may encourage a user of the user device 410 to adhere to a care plan that has been prescribed by a medical provider of the user. In response, the user of the user device 410 provides responses to the queries which may be input via a user interface 412, read by a biometric sensor 414 attached to the user device 410, or the like. In this example, the user device 410 provides a plurality of responses over a period of time (e.g., a few hours, a few days, a few weeks, a month, etc.) which may be analyzed by the software application 422. In this example, the software application 422 may store the responses within a database 424 of the software application 422. Thus, the software application 422 may aggregate the responses together over time and transfer a group of aggregated responses to the AI model 426.

According to various embodiments, the AI model 426 may analyze the group of aggregated responses and determine a status 428 of the user. Here, the AI model 426 may be trained to identify a medical condition or a severity of a medical condition based on a pattern of content, biometric readings, inputs, answers, lack of responses, and the like. In some embodiments, the status 428 determined by the AI model 426 may be used by the software application 422 to "flag" a summary of the user within the inbox of the external viewer.

Figure 5A:
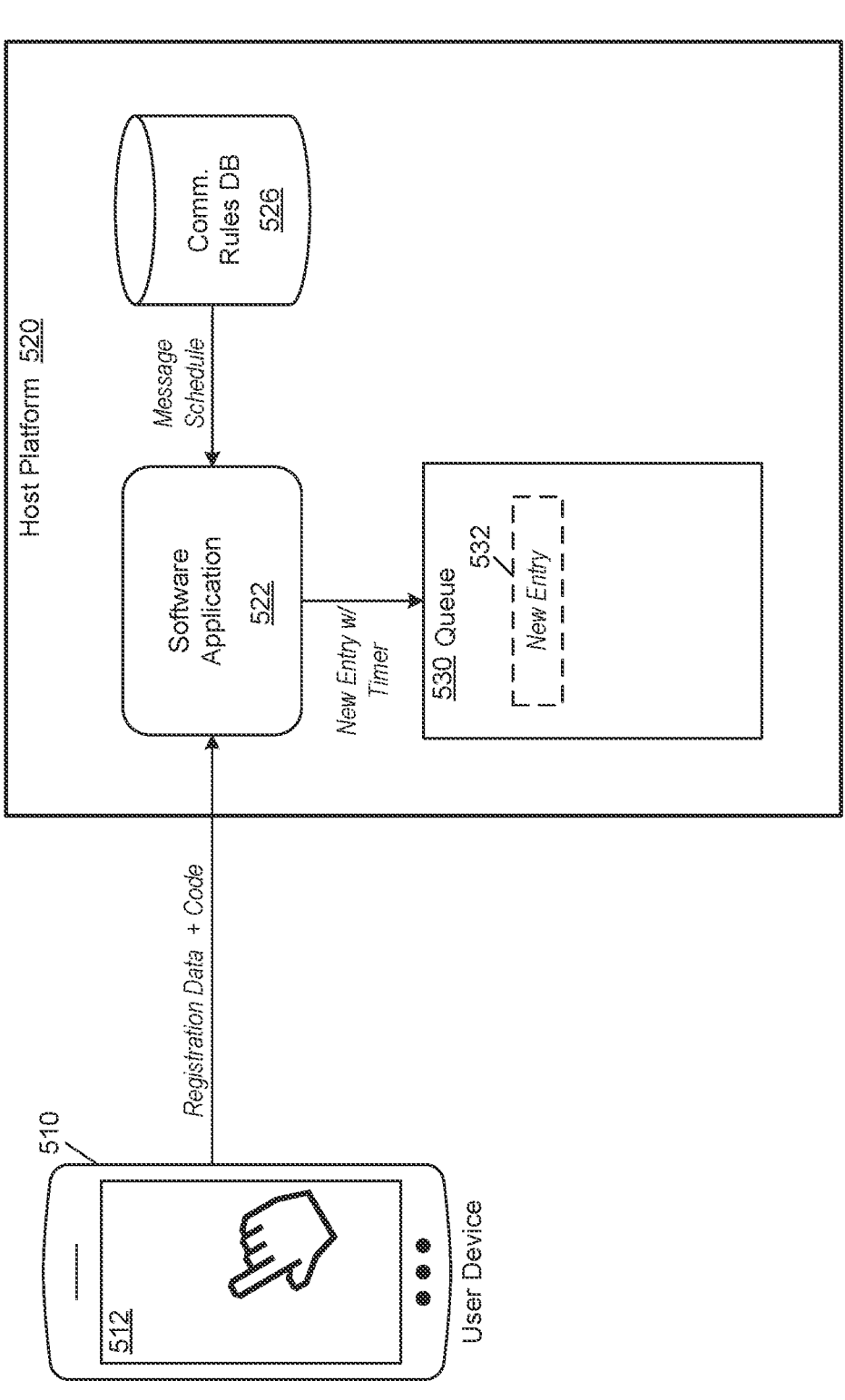
FIGS. 5A-5B are diagrams illustrating a process of dynamically loading application content onto a user device based on registration data according to example embodiments.
Figure 5B:
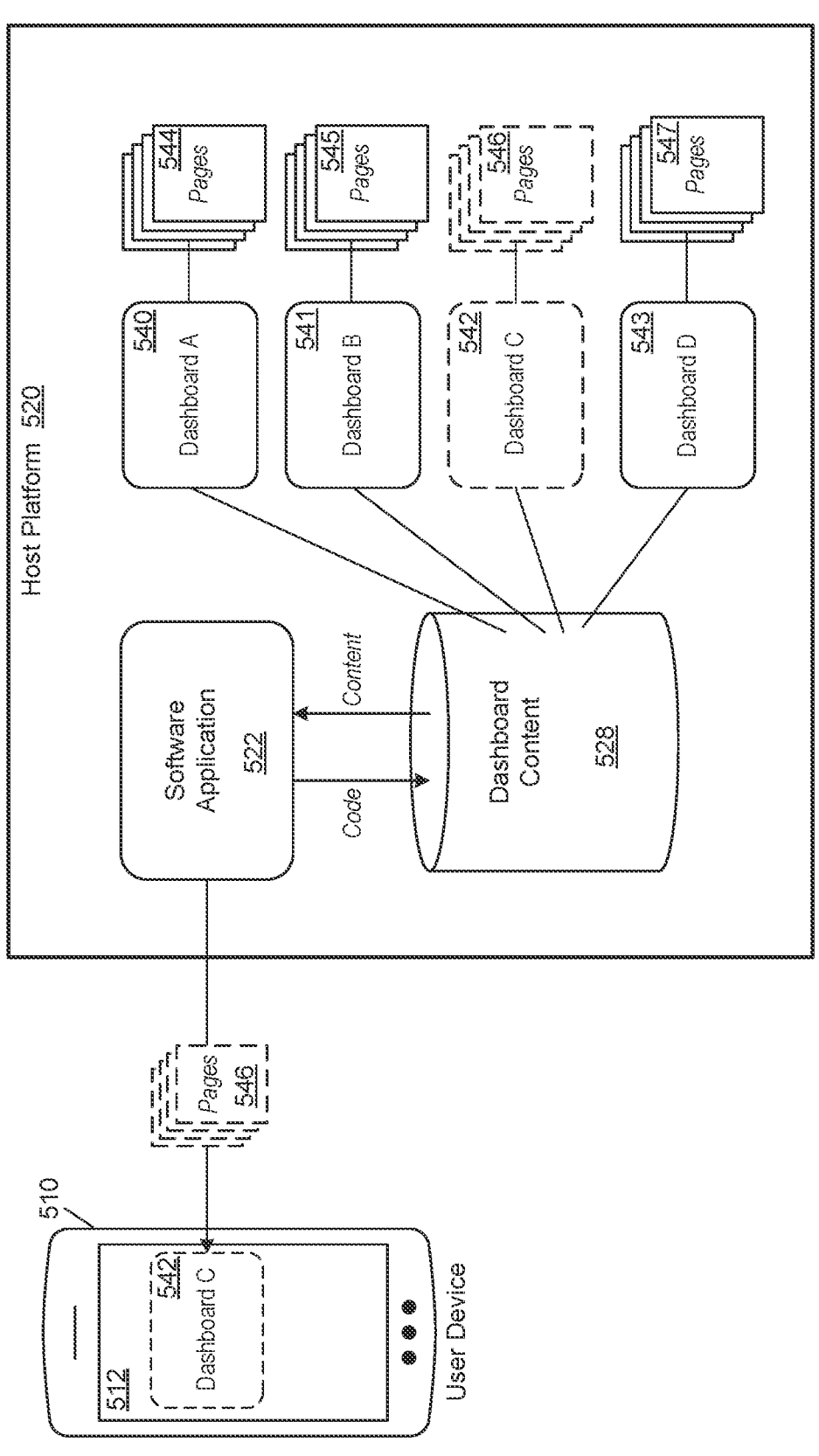

FIGS. 5A-5B illustrate a process of dynamically loading application content onto a user device based on registration data according to example embodiments. For example, FIG. 5A illustrates a process of a user device 510 registering with a software application 522 according to various embodiments. In this example, the software application 522 may be similar to the software application 122 shown in FIG. 1. The software application 522 is hosted by a host platform 520. In addition, the host platform 520 also hosts a queue 530 and a communication rules database 526. The queue 530 holds lifecycle data of a communication sequence assigned to a user device.

According to various embodiments, the user device 510 may provide registration data to the software application 522. The registration process may include the user inputting details such as a username, login credentials, and a code into a user interface 512 of the user device 510. In response, the software application 522 may start a new communication sequence for the user of the user device 510 based on the registration data. For example, the registration data may be used to identify a type of condition that the user has such as diabetes, hypertension, Covid, sleep apnea, etc. Each of these conditions may have a different communication sequence. The communication sequence may ensure that the patient adheres to a prescribed care plan associated with the type of condition. Furthermore, each user with the same condition may receive the same communication sequence. The communication sequence may begin at the time of registration. Here, a new entry 532 may be added to the queue 530 which identifies the user device, the communication sequence, and a timing function.

According to various embodiments, the registration process may be offered in multiple different languages. Here, the user may select a desired language and the screens that are displayed may be displayed with text in the desired language. Here, the software application 522 may provide not only the text but also the video content, downloads, educational materials, etc. in the selected language. Examples of the language include, but are not limited to, English, Spanish, French, and the like.

The queue 530 may hold an entry for each registered user of the software application 522. The entry may include an identifier of a user associated therewith, a communication sequence assigned to the user, and a timer that shows how much time has elapsed since the user registered with the software application. The timer can be used to identify which communication sequence is to be sent, and when, based on communication rules included in a rules database 526. For example, the rules database 526 may identify queries to be sent, the point in time when such queries are to be sent, how long to wait for a response before determining there is no response, and the like. The communication rules may include intervals of time between the different queries.

The code provided by the user may identify a medical facility of the user. Here, the code may be a number or alphanumeric sequence that is input by the user into a field on the user interface 512. As another example, the code may be a QR code or barcode that is scanned by the user device 510 from a picture, wall, document, etc., for example, while visiting the medial facility. In some embodiments, the software application 522 may provide querying, tracking, and real-time viewing services to multiple medical facilities. By providing a code that identifies a particular medical facility, the software application 522 can dynamically add content to the front-end of the software application installed on the user device 510.

For example, FIG. 5B illustrates a process 500B of the software application 522 dynamically populating application content on the user device 510 based on the code that is provided from the user device 510 during the registration process. In this example, the software application 522 includes a database 528 of application content that is assigned to different medical facilities. For example, a first medical facility may be assigned a dashboard 540 and a set of pages of content 544, a second medical facility may be assigned a dashboard 541 and a set of pages of content 545, a third medical facility may be assigned a dashboard 542 and a set of pages 546, and a fourth medical facility may be assigned a dashboard 543 and a set of pages of content 547. The content that is output by the software application 522 to the user device may be in a natural language requested by the user. Here, the software application may provide text, images, videos, etc. in the respective natural language selected by the user creating a feeling of comfortability with the software.

Here, the software application 522 matches the code received from the user device 510 during the registration process to the dashboard 542 and the set of pages 546. In response, the software application 522 may dynamically populate a background of the software application on the user device 510 with the dashboard 542 and integrate the set of pages 546 within a background of the software application 522. The dashboard 542 may include a unique picture or other specific representation that is provided from a specific medical facility/medical provider of the user. Thus, the user can feel comfortable with the messaging with the software application 522 because they know it is an extension of their medical facility. The set of pages 546 may include different pages of content, different links, different educational materials, different contact information, and the like, depending on the medical facility.

Figure 6C:
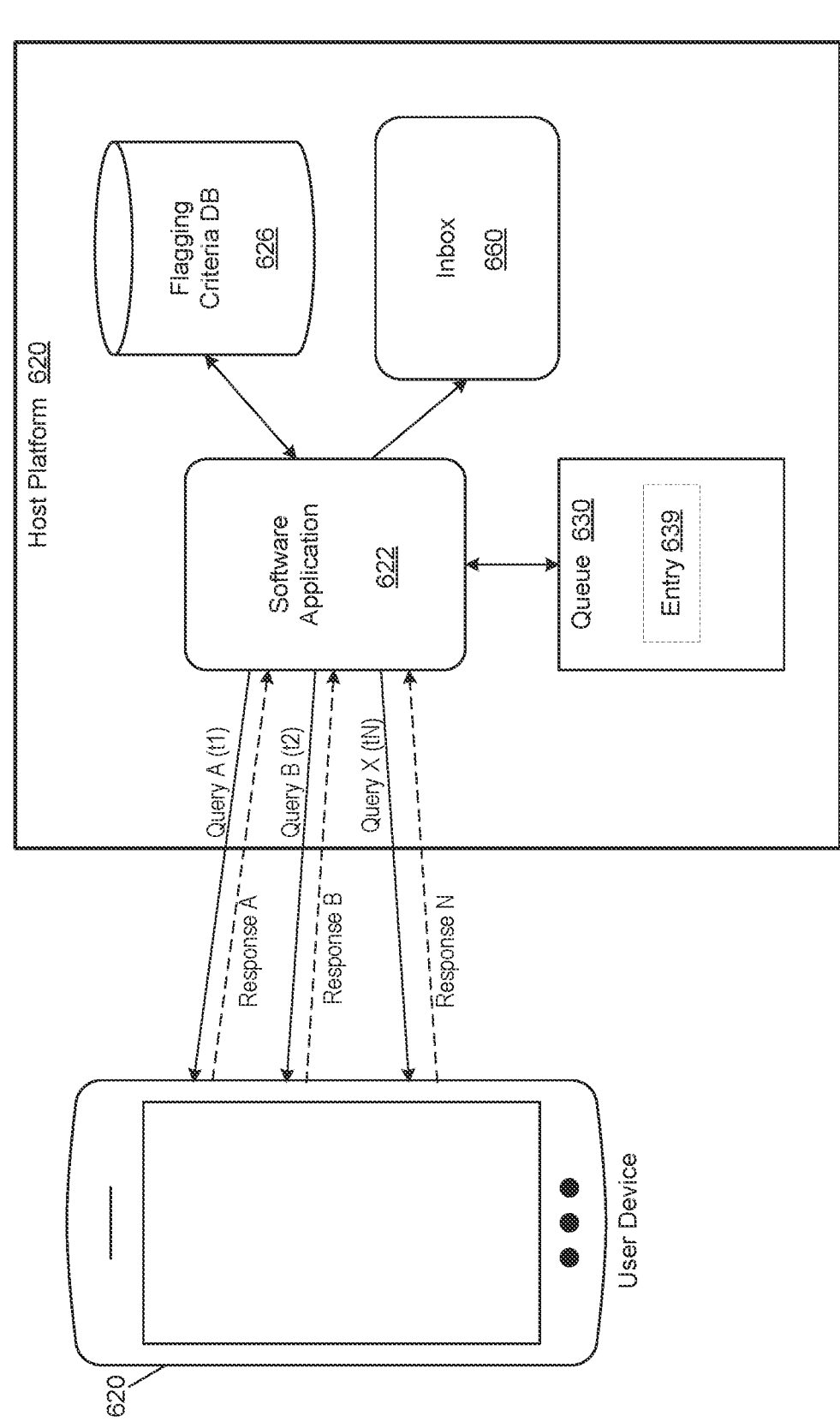

FIGS. 6A-6E illustrate a process of managing a lifecycle of a communication sequence with a user device according to example embodiments. For example, FIG. 6A illustrates a process 600A of a software application 622 hosted by a host platform 620 which manages a queue 630 with communication sequence data of a plurality of users of the software application 622. According to various embodiments, each user of the software application 622 may be assigned a separate respective entry in the queue 630. Here, the queue includes a first entry 631 of a first user, a second entry 632 a second user, a third entry 633 of a third user, a fourth entry 634 of a fourth user, a fifth entry 635 of a fifth user, a sixth entry 636 of a sixth user, and a seventh entry 637 of a seventh user.

Each user has a different time cycle that may be represented using a time-to-live job 638. Each entry within the queue 630 may include an identifier of a user, a timer function (e.g., a time-to-live job 638) that counts down until the communication sequence ends, and information about the communication sequence such as messages to send, intervals of time to wait in between messages being sent, responses expected, and the like. Each time-to-live (TTL) job may be a crone job or something similar. For example, the TTL job may be launched by the software application 622 sending a command to the queue 630 or a service associated with the queue 630 which launches the TTL job. The software application 622 may monitor the communication sequence to be performed for a user, and the timer function (e.g., the TTL job) to determine when and what communication is next to be sent to a user device. In some embodiments, the software application 622 may also rely on rules within a communication rules database 624 that identifies what queries are to be sent, at what timed in the sequence, and the like.

FIG. 6B illustrates a view 600B of a communication schedule 640 that may be integrated into an entry within the queue 630, stored in the communication rules database 624, or the like. Here, the communication schedule 640 includes a sequence of days (e.g., 30 days, etc.) which includes identifiers of days when messages are to be sent, and the type of messages, and days in between (intervals of time) when no messages or other communications are to be sent. The software application 622 may use a TTL job 644 to identify a current point 642 in the communication schedule 640 which is the seventeenth day of the communication sequence 640.

In some embodiments, the TTL job 644 may countdown from the start of the communication sequence to the end of the communication sequence. As another example, the TTL job 644 may count from the start of the communication sequence until the end of the communication sequence. In the example of FIG. 6B, the TTL job 644 counts from the start of the communication sequence 640 to the end. The software application 622 may analyze the timer within the TTL job 644 and determine the current point 642 in the communication sequence. This process may be performed on an iterative basis (e.g., once a day, once an hour, etc.) to identify when a new day has occurred and a new possible message is due to be transmitted to the user device.

According to various embodiments, one or more of the communications in a communication sequence may be related to the patient visiting an outside specialist that is referred by the medical provider managed by the software application 622. In this case, the software application 622 may ensure that the patient is reminded about the referral appointment to the specialist, etc. with additional communications within the communication sequence. Thus, the software application 622 may provide referral tracking functionality. For example, the medical provider may desire to know that the patient set the appointment with the outside referral and that the appointment took place. It can sometimes take months for the specialist to see the person. The software application 622 may send prompts to the patient to find out if the patient has set the date yet, and they can enter the data on the screen they have. As that date approaches, the software application 622 may send reminders to the patient's device to ensure that the patient is reminded of the upcoming appointment. Furthermore, an additional communication can be sent to the patient's device after the scheduled appointment to ensure that the patient made the appointment, or otherwise rescheduled. The software application 622 may dynamically update the communication sequence with additional and/or different communications based on the responses from the patient. Certain types of care management span multiple years. The appointments may be spaced out over months of time. The software application 622 may ensure that these appointments are followed and kept.

FIG. 6C illustrates a process 600C of transmitting queries and other messages to a user device 610 based on queued entry 639 in the queue 630. Here, the queued entry 639 is associated with a communication sequence 650 that identifies when and what queries are to be sent to the user device 610. Accordingly, the software application 622 may analyze the queued entry 639, including a timing function within a TTL job (not shown) and determine when to send queries and what queries to send to the user device 610. In response, the user device 610 may transmit responses to the queries which may be analyzed by the software application 622 to identify whether or not a flag is to be added to the response/summary of the user as further described in FIGS. 7A-7B. Flagging criteria from a database 626 may be used to determine whether to apply a flag to a summary, what kind of flag to apply, and the like. In some embodiments, the responses may be summarized and displayed within an inbox 660. The inbox 660 may be viewable to an external computing system, for example, via a web browser installed on the external computing system. In this case, the inbox 660 may include a uniform resource locator (URL) or other address that can be accessed via an address bar of the web browser on the external device.

FIG. 6D illustrates a process 600D of the software application 622 detecting that the user/patient has failed to respond to a query within a predetermined time period, for example, 12 hours, 24 hours, etc. When the user misses a response, the software application 622 may resend the message a few more times until a flag is raised. For example, if the user responds after two queries (e.g., two days late, etc.), the response is still counted and the user's communication sequence continues uninterrupted/unmodified. Here, the late response is still counted. In FIG. 6D, the software application sends a query to the user device 610 and then waits for a response from the user device 610. If a response is not received within a predetermined period of time, the software application 622 retransmits the same query. This process may be repeated multiple times. If the user has not responded after a predetermined number of re-transmissions (e.g., two, etc.), then a flag may be raised and an alert may be generated.

FIG. 6E illustrates a process 600E of the software application determining that an alert condition has occurred with respect to the user device 610. For example, the alert condition may be a failure to respond to a query, multiple queries, etc. As another example, the alert condition may be the content of a response that is received from the user device 610. For example, the response content may include a description of patient symptoms that invoke the alert. As another example, the response content may include biometric content that is read by a sensing device from the user and which may be above a threshold or below a threshold, thereby triggering an alert/alarm. In this example, the software application 622 may transmit an alert, alarm, etc. to a team member device 670, external management system, etc. The alert may cause a warning on a user interface 672 of the team member device 670. As another example, the alert may cause a bell to ring, lights to flash, etc.

Figure 7A:
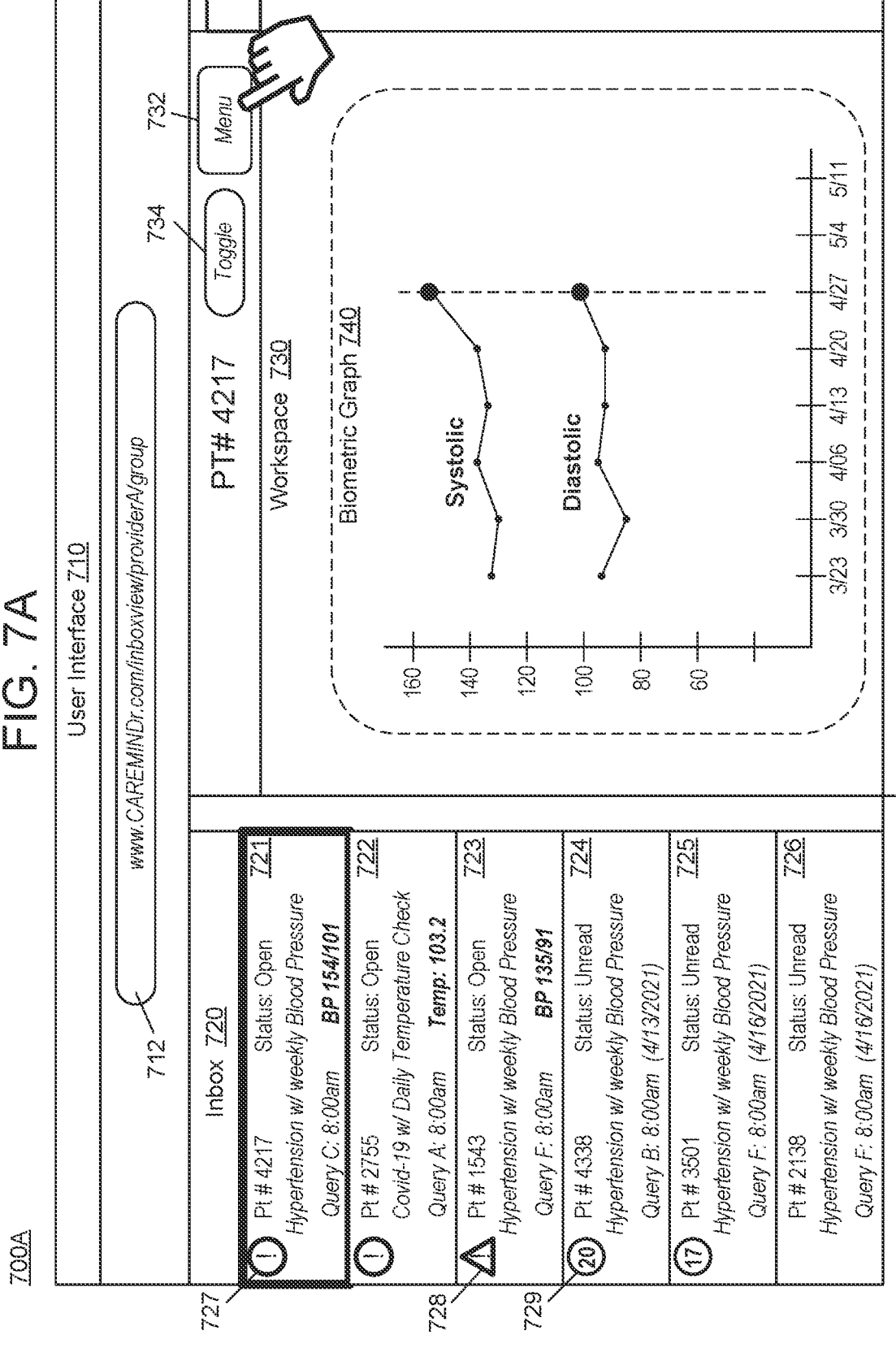
FIGS. 7A-7B are diagrams illustrating a process of providing a real-time inbox view of the status of multiple users according to example embodiments.
Figure 7B:
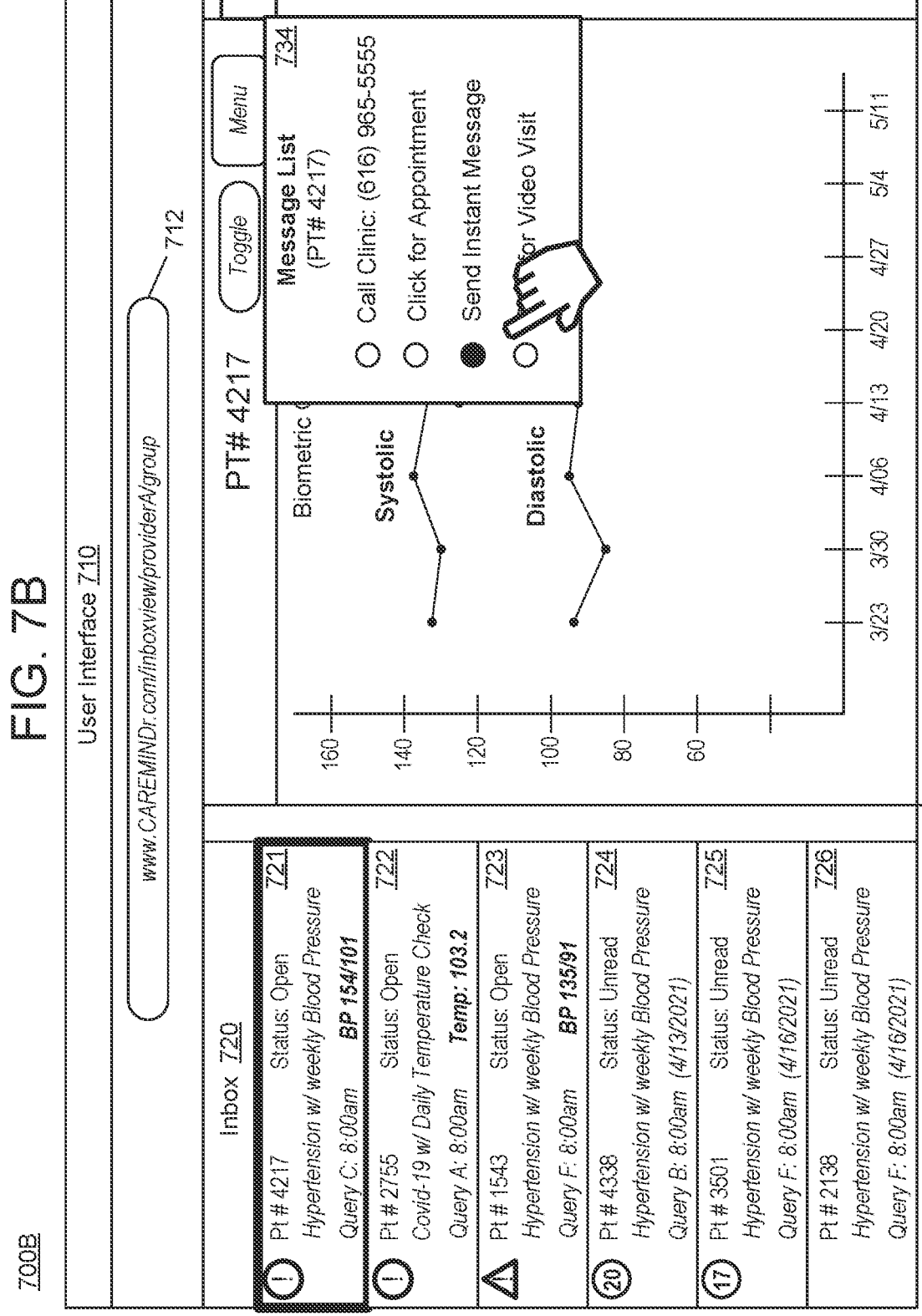

FIGS. 7A-7B illustrate a process of providing a real-time inbox view of the status of multiple users according to example embodiments. For example, FIG. 7A illustrates a view 700A of an inbox 720 that is provided to an external system by the host platform described herein. As an example, the view 700A may be provided by the software application 122 to the external system 130, shown in FIG. 1. In FIG. 7A, a user interface 710 may be output to the external system. The user interface 710 includes an inbox 720 with a list of communications that have been received from a plurality of users/user devices of a provider associated with the external system. In this example, the inbox 720 provides a real-time view of the most-up-to-date status of each of the users.

For example, the inbox 720 includes a summary 721 of a first user, a summary 722 of a second user, a summary 723 of a third user, a summary 724 of a fourth user, a summary 725 of a fifth user, and a summary 726 of a sixth user. According to various embodiments, the software application may arrange the summary within the inbox 720 based on an urgency of the users associated with the summary. The urgency may be identified from a flag such as a flag 727 that is attached to the summary 721. The flag identifies how urgent the summary is and whether a response is needed. The flag 727 may be determined based on rules that are associated with each query that is sent to a user. For example, a particular type of flag may be added to a summary if a biometric measurement of a user is above or below a predetermined threshold.

In the example of FIG. 7A, the flag 727 included in the summary 721 is a most urgent flag indicating that the user is in need of help. Here, a blood pressure reading captured from a user device of the user has indicated that the blood pressure of the user is above a predetermined threshold for safety. To identify which flag to attach to a summary, the software application may use a set of criteria/rules that are previously stored by the software application. Each response from a user may have a set of rules that are applied to identify whether a flag needs to be applied, and which type of flag needs to be applied.

As another example, a flag 728 included in the summary 723 indicates an above average reading that is not yet at the level of the predetermined threshold. This may include comparing the biometric reading to a first threshold and a second threshold, and determining that the biometric reading includes a value that is between the first and second thresholds. As another example, a flag 729 included in the summary 724 indicates that a user corresponding to the summary 724 has not responded to a query. In this example, the flag 729 indicates a lack of response. Furthermore, the software application may display an indicator inside a display area (e.g., inside a perimeter, etc.) of the flag that identifies a number of days or hours that have passed since the lack of response. The rules may identify a predetermined period of time by which a user must respond, for example, 1 day, 12 hours, etc. When the user fails to respond, the software may generate the flag 729 and apply it to a corresponding summary of the user.

In FIG. 7A, the user has selected the summary 721 for further details. In response, the software application may display content about the user corresponding to the summary 721 within a workspace 730 of the user interface 710 next to the inbox 720. In this example, the biometric reading from the user (i.e., blood pressure) has indicated that the user's blood pressure is above a dangerous level. In this example, the software application may display a biometric graph 740 within the workspace 730 which provides the viewer with a trend of the user's blood pressure over time. The user interface 710 also includes a menu button 732 which the viewer can click on to communicate directly with the user (via the user's user device).

In addition, the user interface 710 also includes a toggle button 734 which enables the viewer to change the language (i.e., natural language, etc.) of the user which is shown on the screen. Here, the viewer, such as a member of the care team, may speak a different language than the patient. The viewer can dynamically change/toggle between their desired language and the language of the patient by clicking on the toggle button 734 with an input mechanism such as a finger, a stylus, a keyboard, a mouse, etc. In response, the content shown on the screen may be converted into the language requested. In some embodiments, the toggle may enable switching back and forth between two languages (e.g., English and Spanish, etc.). However, the toggle button may also be associated with a configuration menu (not shown) which enables the viewer to select a different language such as German, French, Japanese, etc. Each of the graphs, messages, page views, etc. that are opened by the viewer may be in the selected language as a result of the viewer selecting the toggle button 734.

For example, FIG. 7B illustrates a view 700B of the user interface 710 after the viewer has clicked on the menu button 732. In this example, a menu 734 is displayed in response to the menu button 732 being pressed. The menu 734 provides the viewer of the external system with the ability to connect directly to the user device of the user who's information is included in the summary. For example, the menu 734 may provide an instant messaging function that enables the viewer to send an instant message from the menu 734 included in the user interface 710 to a user device of the user. The message may be displayed within a front-end of the software application installed on the user device. Thus, the provider can directly communicate with the user when the user is experiencing a dangerous condition. As another example, the menu 734 enables the user to call the user on the user device, set up an appointment for the user with a medical provider, set up a video call with the user, and the like.

FIG. 8 illustrates a process 800 of generating documented evidence for a provider according to example embodiments. Evidence-based care is different and describes a pathway that has passed peer review analysis and is being promoted as the right way to do something in the industry. Examples of evidence-based care include a recommended medication and dosage to be used in patients based on their physical characteristics, a frequency that certain monitoring lab tests should be performed, complications or contraindications that commonly occur and which need specific monitoring, and the like. In the example embodiments, a software application 822 hosted by a host platform 820 may receive responses to queries from one or more patient devices, for example, a user device 810. The responses may include text content input via a user interface 812 of the user device 810. As another example, the responses may include sensor data, biometric data, etc. which may be captured with one or more sensors 814. Here, the software application 822 may receive the responses, and store them in a data store 824. For example, the software application 822 may aggregate responses together within the data store 824 to generate evidence necessary for a medical provider to receive payment from an agency. In this example, the agency may require proof in the form of message responses, biometric readings, etc. to prove that the medical provider is making an impact on the patient.

According to various embodiments, the software application 822 may generate a financial accounting report 826 with a code 827 (e.g., a billing code such as CPT codes, etc.) and insert the code 827 into the financial accounting report 826. The report may include a digital document that can be transferred via email, or the like, and which can be submitted by the medical provider to obtain payment from an insurance company, authoritative agency, or the like.

As an example, a common practice terminology (CPT) code (CPT99454) is a code that enables a medical provider to be paid. The software application 822 may prompt a patient and create "proof" of this response, including whether the response is normal or abnormal. In this case, payment may depend on the value created (e.g., an improvement in a patient's biometric readings for hypertension, diabetes, etc.) These a metrically driven. In some medical issues there are bands of values (guidelines of what is controlled and what is not controlled). The doctor signs up and gets judged based on what percentage of their patients are meeting the necessary biometric readings. The software gathers the data necessary for the doctors to create proof of this value service and adds it to the financial accounting report 826.

Figure 9:
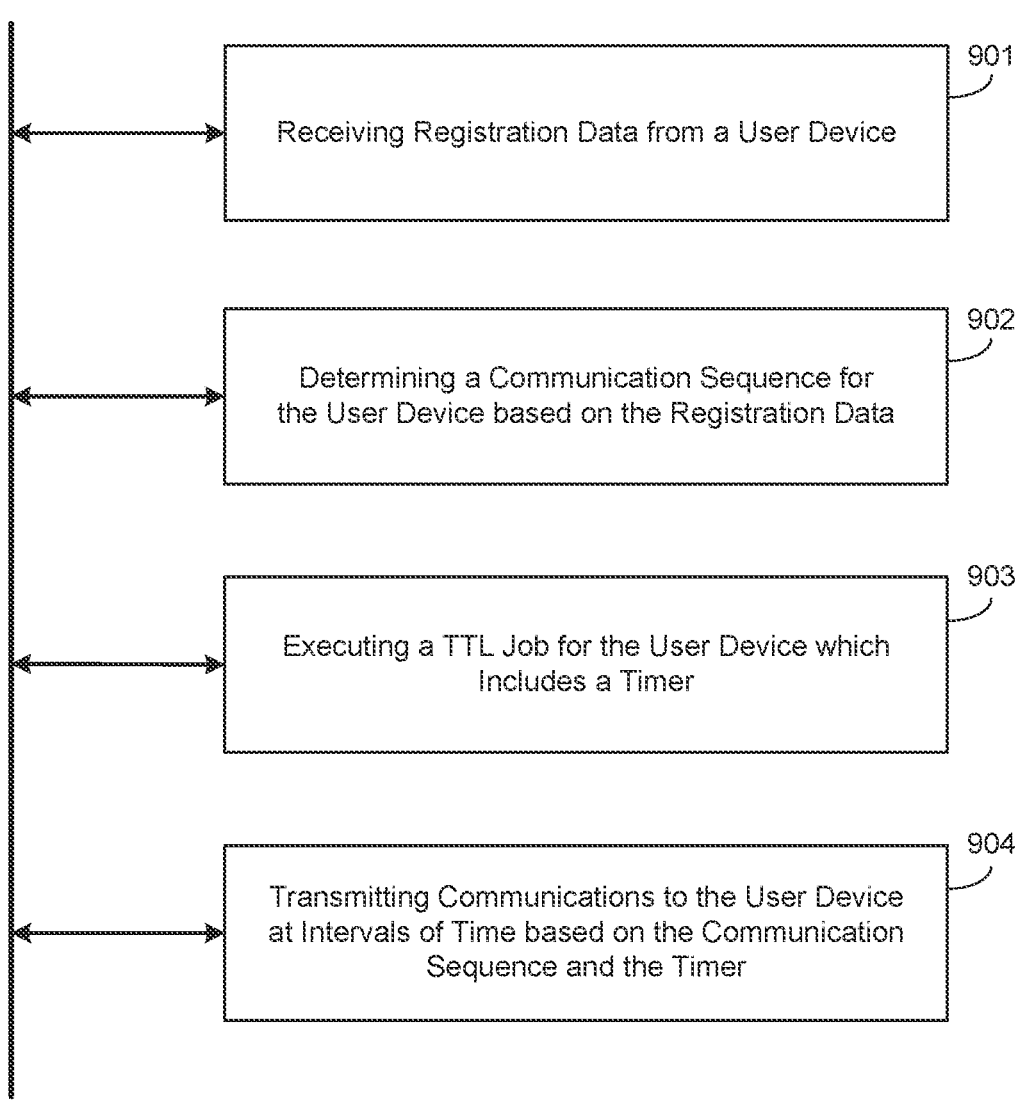
FIG. 9 is a diagram illustrating a method of executing a communication sequence with a user device according to example embodiments.

FIG. 9 illustrates a method 900 of executing a communication sequence with a user device according to example embodiments. For example, the method 900 may be performed by a host platform such as a web server, cloud platform, on-premises server, or the like. Referring to FIG. 9, in 901, the method may include receiving registration data from a software application installed on a user device, where the software application is hosted by a host platform. The registration data may include a code that uniquely identifies a service provider of a user of the user device. The code may be input on a user interface of the user device, scanned by the user device (e.g., via a barcode, QR code, etc.), and the like.

In 902, the method may include determining a communication sequence for a user of the user device which includes multiple communications spaced apart by intervals of time based on the registration data received from the software application. In 903, the method may include executing a time-to-live (TTL) job for the user which includes a timer that is based on the intervals of time included in the communication sequence. In 904, the method may include transmitting communications to the user device at the intervals of time based on time elapsing on the timer included in the TTL job.

In some embodiments, the method may further include establishing a network communication channel between the host platform and an external computing system, receiving a response to a communication from the user device, determining a status of the user based on the communication, and displaying a summary of the communication within an inbox of the external computing system via the network communication channel. In some embodiments, the method may further include receiving a plurality of responses from a plurality of user devices, filtering the plurality of responses to identify a subset of responses that are more urgent based on content included in the subset of responses, and displaying the subset of responses that are more urgent at a top of the inbox. In some embodiments, the method may further include receiving an input on a user interface of the external computing system with respect to the summary of the communication, and in response, displaying a menu with an instant messaging window next to the inbox within the user interface of the external computing system which enables the external computing system to input and send a message to the user device.

In some embodiments, the method may further include detecting that the user device failed to respond to a communication based on the timer included in the TTL job, and in response, flagging the communication with an alert, and storing the flagged communication within a user profile of the user. In some embodiments, the transmitting may include transmitting a communication to the user device at an interval of time specified by predefined timing rules stored within a storage of the host platform and a current time value on the TTL job.

In some embodiments, the method may further include dynamically selecting a dashboard background for display on the user device from among a plurality of dashboard backgrounds based on a code included in the registration data, and populating a user interface of the user device with the dashboard background prior to transmitting the communications to the user device. In some embodiments, the method may further include dynamically selecting a set of pages for display on the user device from among a plurality of sets of pages based on a code included in the registration data, and populating a user interface of the user device with the set of pages in a background, and a menu that enables the user device to select a page from among the set of pages.

The above embodiments may be implemented in hardware, in a computer program executed by a processor, in firmware, or in a combination of the above. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example, FIG. 10 illustrates an example computer system architecture, which may represent or be integrated in any of the above-described components, etc.

Figure 10:
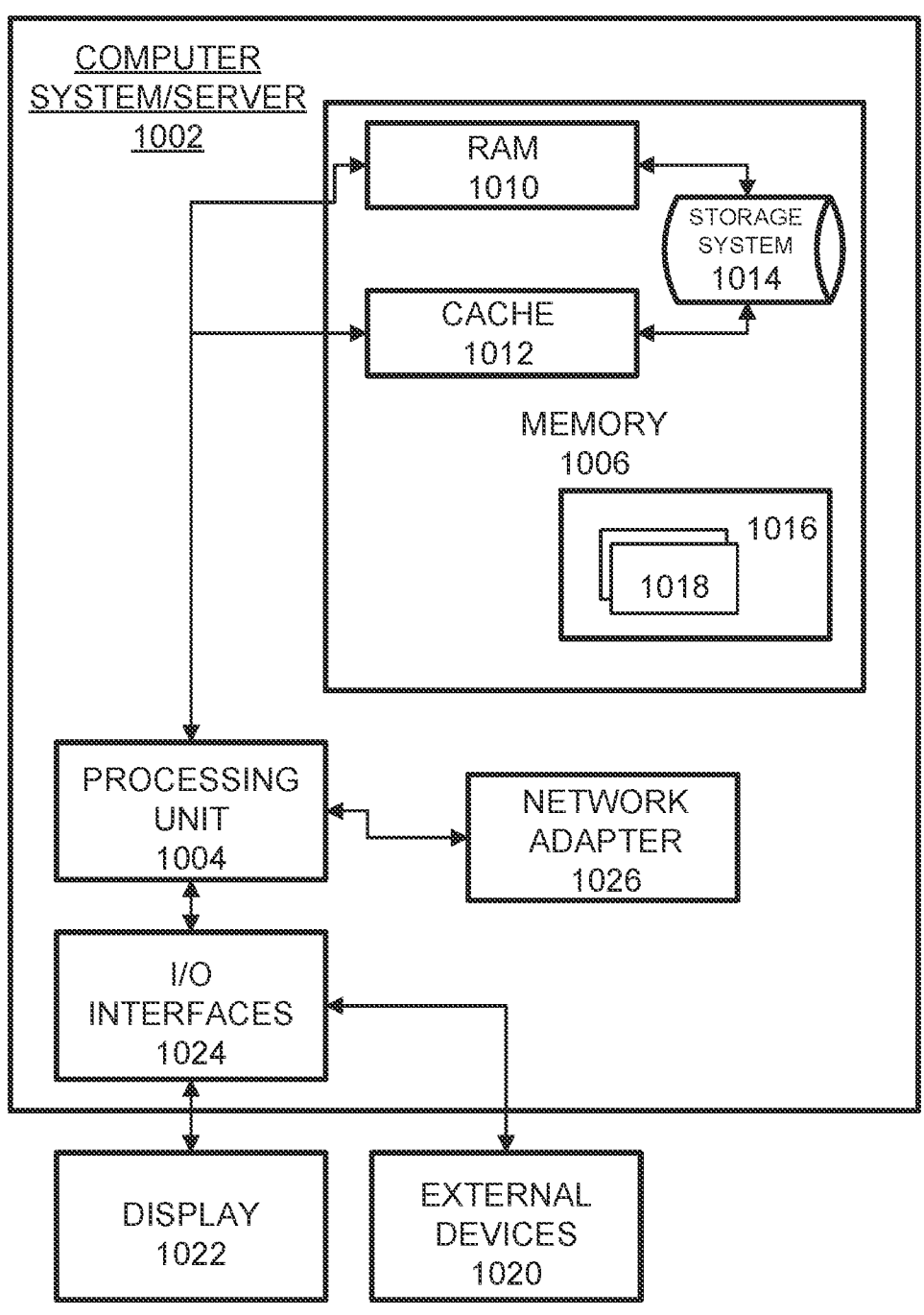
FIG. 10 is a diagram illustrating a computing system that may be used in any of the example embodiments described herein.

FIG. 10 illustrates an example system 1000 that supports one or more of the example embodiments described and/or depicted herein. The system 1000 comprises a computer system/server 1002, which is operational with numerous other general purpose or special purpose computing system environments or configurations. Examples of well-known computing systems, environments, and/or configurations that may be suitable for use with computer system/server 1002 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 1002 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 1002 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 10, computer system/server 1002 in the example system 1000 is shown in the form of a general-purpose computing device. The components of computer system/server 1002 may include, but are not limited to, one or more processors or processing units (processor 1004), a system memory 1006, and a bus that couples various system components including the system memory 1006 to the processor 1004.

The bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 1002 typically includes a variety of computer system readable media. Such media may be any available media that is accessible by computer system/server 1002, and it includes both volatile and non-volatile media, removable and non-removable media. The system memory 1006, in one embodiment, implements the flow diagrams of the other figures. The system memory 1006 can include computer system readable media in the form of volatile memory, such as random-access memory (RAM) 1010 and/or cache memory 1012. Computer system/server 1002 may further include other removable/non-removable, volatile/non-volatile computer system storage media. By way of example only, storage system 1014 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus by one or more data media interfaces. As will be further depicted and described below, the system memory 1006 may include at least one program product having a set (e.g., at least one) of program modules that are configured to carry out the functions of various embodiments of the application.

Program/utility 1016, having a set (at least one) of program modules 1018, may be stored in the system memory 1006 by way of example, and not limitation, as well as an operating system, one or more application programs, other program modules, and program data. Each of the operating system, one or more application programs, other program modules, and program data or some combination thereof, may include an implementation of a networking environment. Program modules 1018 generally carry out the functions and/or methodologies of various embodiments of the application as described herein.

As will be appreciated by one skilled in the art, aspects of the present application may be embodied as a system, method, or computer program product. Accordingly, aspects of the present application may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present application may take the form of a computer program product embodied in one or more computer readable medium(s) having computer readable program code embodied thereon.

Computer system/server 1002 may also communicate with one or more external devices 1020 such as a keyboard, a pointing device, a display 1022, etc.; one or more devices that enable a user to interact with computer system/server 1002; and/or any devices (e.g., network card, modem, etc.) that enable computer system/server 1002 to communicate with one or more other computing devices. Such communication can occur via I/O interfaces 1024. Still yet, computer system/server 1002 can communicate with one or more networks such as a local area network (LAN), a general wide area network (WAN), and/or a public network (e.g., the Internet) via network adapter 1026. As depicted, network adapter 1026 communicates with the other components of computer system/server 1002 via a bus. It should be understood that although not shown, other hardware and/or software components could be used in conjunction with computer system/server 1002. Examples include, but are not limited to: microcode, device drivers, redundant processing units, external disk drive arrays, RAID systems, tape drives, and data archival storage systems, etc.

Although an exemplary embodiment of at least one of a system, method, and computer readable medium has been illustrated in the accompanying drawings and described in the foregoing detailed description, it will be understood that the application is not limited to the embodiments disclosed but is capable of numerous rearrangements, modifications, and substitutions as set forth and defined by the following claims. For example, the system's capabilities of the various figures can be performed by one or more of the modules or components described herein or in a distributed architecture and may include a transmitter, receiver, or pair of both. For example, all or part of the functionality performed by the individual modules may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via a plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone, or any other suitable computing device, or combination of devices. Presenting the above-described functions as being performed by a "system" is not intended to limit the scope of the present application in any way but is intended to provide one example of many embodiments. Indeed, methods, systems, and apparatuses disclosed herein may be implemented in localized and distributed forms consistent with computing technology.

It should be noted that some of the system features described in this specification have been presented as modules in order to more particularly emphasize their implementation independence. For example, a module may be implemented as a hardware circuit comprising custom very large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction or many instructions and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations, including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed but is merely representative of selected embodiments of the application.

One having ordinary skill in the art will readily understand that the above may be practiced with steps in a different order and/or with hardware elements in configurations that are different from those which are disclosed. Therefore, although the application has been described based upon these preferred embodiments, it would be apparent to those of skill in the art that certain modifications, variations, and alternative constructions would be apparent.

While preferred embodiments of the present application have been described, it is to be understood that the embodiments described are illustrative only, and the scope of the application is to be defined solely by the appended claims when considered with a full range of equivalents and modifications (e.g., protocols, hardware devices, software platforms, etc.) thereto.

What is claimed is:

1. An apparatus comprising:
a memory; and
a processor coupled to the memory, the processor configured to receive registration data from a software application installed on a user device, where the software application is hosted by a host platform, determine a communication sequence for a user of the user device which includes multiple communications spaced apart by intervals of time based on the registration data received from the software application, execute a time-to-live (TTL) job for the user which includes a timer that is based on the intervals of time included in the communication sequence, and transmit communications to the user device at the intervals of time based on time elapsing on the timer included in the TTL job, wherein a set of pages are dynamically selected for display on the user device from among a plurality of sets of pages based on a code included in the registration data, wherein a user interface of the user device is populated with the set of pages in a background and a menu that enables the user device to select a page from among the set of pages.

2. The apparatus of claim 1, wherein the processor is further configured to establish a network communication channel between the host platform and an external computing system, receive a response to a communication from the user device, determine a status of the user based on the communication, and display a summary of the communication within an inbox of the external computing system via the network communication channel.

3. The apparatus of claim 2, wherein the processor is configured to receive a plurality of responses from a plurality of user devices, filter the plurality of responses to identify a subset of responses that are more urgent based on content included in the subset of responses, and display the subset of responses that are more urgent at a top of the inbox.

4. The apparatus of claim 2, wherein the processor is further configured to receive an input on a user interface of the external computing system with respect to the summary of the communication, and in response, display a menu with an instant messaging window next to the inbox within the user interface of the external computing system which enables the external computing system to input and send a message to the user device.

5. The apparatus of claim 1, wherein the processor is further configured to detect that the user device failed to respond to a communication based on the timer included in the TTL job, and in response, flag the communication with an alert and store the flagged communication within a user profile of the user.

6. The apparatus of claim 1, wherein the processor is configured to transmit a communication to the user device at an interval of time specified by predefined timing rules stored within a storage of the host platform and a current time value on the TTL job.

7. The apparatus of claim 1, wherein the processor is further configured to dynamically select a dashboard background for display on the user device from among a plurality of dashboard backgrounds based on a code included in the registration data and populate a user interface of the user device with the dashboard background prior to transmitting the communications to the user device.

8. A method comprising:
receiving registration data from a software application installed on a user device, where the software application is hosted by a host platform;

determining a communication sequence for a user of the user device which includes multiple communications spaced apart by intervals of time based on the registration data received from the software application;

executing a time-to-live (TTL) job for the user which includes a timer that is based on the intervals of time included in the communication sequence; and transmitting communications to the user device at the intervals of time based on time elapsing on the timer included in the TTL job, wherein a set of pages are dynamically selected for display on the user device from among a plurality of sets of pages based on a code included in the registration data, wherein a user interface of the user device is populated with the set of pages in a background and a menu that enables the user device to select a page from among the set of pages.

9. The method of claim 8, wherein the method further comprises dynamically selecting a dashboard background for display on the user device from among a plurality of dashboard backgrounds based on a code included in the registration data, and populating a user interface of the user device with the dashboard background prior to transmitting the communications to the user device.

10. The method of claim 8, wherein the method further comprises establishing a network communication channel between the host platform and an external computing system, receiving a response to a communication from the user device, determining a status of the user based on the communication, and displaying a summary of the communication within an inbox of the external computing system via the network communication channel.

11. The method of claim 10, wherein the method further comprises receiving a plurality of responses from a plurality of user devices, filtering the plurality of responses to identify a subset of responses that are more urgent based on content included in the subset of responses, and displaying the subset of responses that are more urgent at a top of the inbox.

12. The method of claim 10, wherein the method further comprises receiving an input on a user interface of the external computing system with respect to the summary of the communication, and in response, displaying a menu with an instant messaging window next to the inbox within the user interface of the external computing system which enables the external computing system to input and send a message to the user device.

13. The method of claim 8, wherein the method further comprises detecting that the user device failed to respond to a communication based on the timer included in the TTL job, and in response, flagging the communication with an alert, and storing the flagged communication within a user profile of the user.

14. The method of claim 8, wherein the transmitting comprises transmitting a communication to the user device at an interval of time specified by predefined timing rules stored within a storage of the host platform and a current time value on the TTL job.

15. A non-transitory computer-readable storage medium comprising instructions which when executed by a processor cause the processor to perform:

receiving registration data from a software application installed on a user device, where the software application is hosted by a host platform;

determining a communication sequence for a user of the user device which includes multiple communications spaced apart by intervals of time based on the registration data received from the software application;

executing a time-to-live (TTL) job for the user which includes a timer that is based on the intervals of time included in the communication sequence; and transmitting communications to the user device at the intervals of time based on time elapsing on the timer included in the TTL job, wherein a set of pages are dynamically selected for display on the user device from among a plurality of sets of pages based on a code included in the registration data, wherein a user interface of the user device is populated with the set of pages in a background and a menu that enables the user device to select a page from among the set of pages.

16. The non-transitory computer-readable storage medium of claim 15, wherein the processor is further configured to perform establishing a network communication channel between the host platform and an external computing system, receiving a response to a communication from the user device, determining a status of the user based on the communication, and displaying a summary of the communication within an inbox of the external computing system via the network communication channel.

17. The non-transitory computer-readable storage medium of claim 16, wherein the processor is further configured to perform receiving a plurality of responses from a plurality of user devices, filtering the plurality of responses to identify a subset of responses that are more urgent based on content included in the subset of responses, and displaying the subset of responses that are more urgent at a top of the inbox.

18. The non-transitory computer-readable storage medium of claim 15, wherein the processor is further configured to perform detecting that the user device failed to respond to a communication based on the timer included in the TTL job, and in response, flagging the communication with an alert, and storing the flagged communication within a user profile of the user.

\*  \*  \*  \*  \*